(12) United States Patent
Tendler et al.

(10) Patent No.: US 11,202,905 B2
(45) Date of Patent: *Dec. 21, 2021

(54) ELECTRICAL SUBSTANCE CLEARANCE FROM THE BRAIN

(71) Applicant: RAINBOW MEDICAL LTD., Herzliya (IL)

(72) Inventors: Alex Tendler, Haifa (IL); Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 174 days.

This patent is subject to a terminal disclaimer.

(21) Appl. No.: 16/353,407

(22) Filed: Mar. 14, 2019

(65) Prior Publication Data

US 2019/0282807 A1    Sep. 19, 2019

Related U.S. Application Data

(60) Provisional application No. 62/642,663, filed on Mar. 14, 2018.

(51) Int. Cl.
*A61N 1/00* (2006.01)
*A61N 1/20* (2006.01)
(Continued)

(52) U.S. Cl.
CPC ........... *A61N 1/205* (2013.01); *A61N 1/0529* (2013.01); *A61N 1/0534* (2013.01); *A61N 1/306* (2013.01);
(Continued)

(58) Field of Classification Search
CPC .......................... A61N 1/0534; A61N 1/36067
See application file for complete search history.

(56) References Cited

U.S. PATENT DOCUMENTS

| 4,044,774 A | 8/1977 | Corbin et al. |
| 4,503,863 A | 3/1985 | Katims |

(Continued)

FOREIGN PATENT DOCUMENTS

| JP | 2004-321242 A | 11/2004 |
| JP | 2007-501067 A | 1/2007 |

(Continued)

OTHER PUBLICATIONS

An Office Action dated Mar. 6, 2020, which issued during the prosecution of U.S. Appl. No. 15/618,325.

(Continued)

*Primary Examiner* — Rex R Holmes
*Assistant Examiner* — Sana Sahand
(74) *Attorney, Agent, or Firm* — Sughrue Mion, PLLC

(57) ABSTRACT

An electrical brain treatment system includes a parenchymal electrode, configured to be implanted in direct physical contact with brain parenchyma or meninges of the brain of a subject identified as at risk of or suffering from a disease; and a cerebrospinal fluid (CSF) electrode, configured to be implanted in a CSF-filled space selected from a ventricular system and a subarachnoid space. Control circuitry is electrically coupled to the parenchymal electrode and the CSF electrode, and is configured to clear a substance from the brain parenchyma into the CSF-filled space of the brain by applying direct current between the parenchymal electrode and the CSF electrode as a series of pulses, with an average amplitude of between 0.25 and 0.5 mA, an average pulse width of between 0.5 and 2 ms, and an average frequency of between 1 and 5 Hz. Other embodiments are also described.

32 Claims, 12 Drawing Sheets

(51) Int. Cl.
*A61N 1/36* (2006.01)
*A61N 1/05* (2006.01)
*A61N 1/30* (2006.01)
*A61N 1/32* (2006.01)

(52) U.S. Cl.
CPC ......... *A61N 1/327* (2013.01); *A61N 1/36067* (2013.01); *A61N 1/36082* (2013.01)

(56) References Cited

U.S. PATENT DOCUMENTS

| | | | |
|---|---|---|---|
| 5,088,977 A | 2/1992 | Sibalis | |
| 5,121,754 A | 6/1992 | Mullett | |
| 5,433,739 A | 7/1995 | Sluijter et al. | |
| 5,529,574 A | 6/1996 | Frackelton | |
| 5,792,100 A | 8/1998 | Shantha | |
| 5,911,223 A | 6/1999 | Weaver et al. | |
| 5,938,690 A | 8/1999 | Law et al. | |
| 6,041,252 A | 3/2000 | Walker et al. | |
| 6,146,380 A | 11/2000 | Racz et al. | |
| 6,161,047 A | 12/2000 | King et al. | |
| 6,360,750 B1 | 3/2002 | Gerber et al. | |
| 6,567,702 B1 | 5/2003 | Nekhendzy et al. | |
| 6,591,138 B1 | 7/2003 | Fischell et al. | |
| 6,602,248 B1 | 8/2003 | Sharps et al. | |
| 6,620,155 B2 | 9/2003 | Underwood et al. | |
| 6,941,172 B2 | 9/2005 | Nachum | |
| 6,997,941 B2 | 2/2006 | Sharkey et al. | |
| 7,013,177 B1 | 3/2006 | Whitehurst et al. | |
| 7,120,489 B2 | 10/2006 | Shalev et al. | |
| 7,217,351 B2 | 5/2007 | Krumme | |
| 7,223,227 B2 | 5/2007 | Pflueger | |
| 7,270,659 B2 | 9/2007 | Ricart et al. | |
| 7,317,947 B2 | 1/2008 | Wahlstrand et al. | |
| 7,398,121 B2 | 7/2008 | Matsumura et al. | |
| 7,509,171 B2 | 3/2009 | DiMauro | |
| 7,640,062 B2 | 12/2009 | Shalev | |
| 7,818,063 B2 | 10/2010 | Wallace et al. | |
| 7,831,306 B2 | 11/2010 | Finch et al. | |
| 7,860,569 B2 | 12/2010 | Solberg et al. | |
| 8,060,207 B2 | 11/2011 | Wallace et al. | |
| 8,190,248 B2 | 5/2012 | Besio et al. | |
| 8,353,853 B1 | 1/2013 | Kyle et al. | |
| 8,457,761 B2 | 6/2013 | Wariar | |
| 8,577,469 B2 | 11/2013 | Gross | |
| 8,676,348 B2 | 3/2014 | Gross | |
| 8,731,674 B2 | 5/2014 | Wallace et al. | |
| 9,616,221 B2 | 4/2017 | Gross | |
| 9,724,513 B2 | 8/2017 | Lane et al. | |
| 9,724,515 B2 | 8/2017 | Fostick et al. | |
| 9,731,122 B2 | 8/2017 | Gross | |
| 10,173,063 B2* | 1/2019 | Fostick | A61N 1/36082 |
| 10,398,884 B2 | 9/2019 | Lad et al. | |
| 10,569,086 B2* | 2/2020 | Fostick | A61N 1/0534 |
| 10,898,716 B2* | 1/2021 | Fostick | A61N 1/36082 |
| 2002/0151948 A1 | 10/2002 | King et al. | |
| 2002/0183683 A1 | 12/2002 | Lerner | |
| 2003/0130707 A1 | 7/2003 | Gan et al. | |
| 2003/0158589 A1 | 8/2003 | Katsnelson | |
| 2003/0216792 A1 | 11/2003 | Levin et al. | |
| 2003/0225331 A1 | 12/2003 | Diederich et al. | |
| 2004/0002746 A1 | 1/2004 | Ryan et al. | |
| 2004/0019381 A1 | 1/2004 | Pflueger | |
| 2004/0049180 A1 | 3/2004 | Sharps et al. | |
| 2004/0116977 A1 | 6/2004 | Finch et al. | |
| 2004/0210209 A1 | 10/2004 | Yeung et al. | |
| 2005/0010205 A1 | 1/2005 | Hovda et al. | |
| 2005/0021104 A1 | 1/2005 | DiLorenzo | |
| 2005/0119650 A1 | 6/2005 | Sanders et al. | |
| 2005/0137646 A1* | 6/2005 | Wallace | A61N 1/0529 607/45 |
| 2005/0137647 A1 | 6/2005 | Wallace et al. | |
| 2005/0159790 A1 | 7/2005 | Shalev | |
| 2005/0187589 A1* | 8/2005 | Wallace | A61N 1/36082 607/45 |
| 2005/0203599 A1 | 9/2005 | Garabedian et al. | |
| 2005/0203600 A1 | 9/2005 | Wallace et al. | |
| 2005/0203602 A1 | 9/2005 | Wallace et al. | |
| 2005/0222647 A1* | 10/2005 | Wahlstrand | A61N 1/0529 607/72 |
| 2005/0277996 A1 | 12/2005 | Podhajsky et al. | |
| 2006/0030895 A1 | 2/2006 | Simon et al. | |
| 2006/0106430 A1 | 5/2006 | Fowler et al. | |
| 2006/0224223 A1 | 10/2006 | Podhajsky et al. | |
| 2006/0293723 A1 | 12/2006 | Whitehurst et al. | |
| 2007/0000784 A1 | 1/2007 | Paul et al. | |
| 2007/0073402 A1 | 3/2007 | Vresilovic et al. | |
| 2007/0162086 A1 | 7/2007 | Dilorenzo | |
| 2007/0213700 A1 | 9/2007 | Davison et al. | |
| 2007/0255338 A1 | 11/2007 | Wahlstrand | |
| 2008/0009927 A1 | 1/2008 | Vilims | |
| 2008/0119907 A1 | 5/2008 | Stahmann | |
| 2008/0260542 A1 | 10/2008 | Nishikawa et al. | |
| 2009/0112278 A1 | 4/2009 | Wingeier et al. | |
| 2009/0125080 A1* | 5/2009 | Montgomery, Jr. | A61N 1/0534 607/45 |
| 2009/0126813 A1 | 5/2009 | Yanagisawa et al. | |
| 2009/0131850 A1 | 5/2009 | Geiger | |
| 2009/0312816 A1 | 12/2009 | Gross | |
| 2010/0217369 A1 | 8/2010 | Gross | |
| 2010/0324441 A1 | 12/2010 | Hargrove et al. | |
| 2011/0046540 A1 | 2/2011 | Alterman et al. | |
| 2011/0054518 A1 | 3/2011 | Carbunaru et al. | |
| 2011/0054567 A1* | 3/2011 | Lane | A61B 5/1118 607/59 |
| 2011/0160638 A1 | 6/2011 | Mauge et al. | |
| 2011/0160797 A1 | 6/2011 | Makous et al. | |
| 2012/0053659 A1 | 3/2012 | Molnar et al. | |
| 2012/0203307 A1 | 8/2012 | Schroeppel et al. | |
| 2013/0066392 A1 | 3/2013 | Simon et al. | |
| 2013/0102952 A1 | 4/2013 | Gross | |
| 2013/0166006 A1 | 6/2013 | Williams | |
| 2013/0289385 A1* | 10/2013 | Lozano | A61B 5/055 600/411 |
| 2014/0058189 A1 | 2/2014 | Stubbeman | |
| 2014/0088672 A1 | 3/2014 | Bedenbaugh | |
| 2014/0207224 A1 | 7/2014 | Simon | |
| 2014/0257168 A1 | 9/2014 | Gill | |
| 2014/0324128 A1* | 10/2014 | Gross | A61N 1/0536 607/62 |
| 2015/0011927 A1 | 1/2015 | Hua | |
| 2015/0119898 A1 | 4/2015 | Desalles et al. | |
| 2016/0331970 A1* | 11/2016 | Lozano | A61N 1/36146 |
| 2017/0007823 A1 | 1/2017 | Gross | |
| 2017/0056642 A1 | 3/2017 | Moffitt et al. | |
| 2017/0120053 A1* | 5/2017 | Fostick | A61N 1/327 |
| 2017/0182317 A1 | 6/2017 | Gross et al. | |
| 2017/0296821 A1 | 10/2017 | Fostick et al. | |
| 2018/0071523 A1 | 3/2018 | Gross et al. | |
| 2018/0193646 A1 | 7/2018 | Fostick et al. | |
| 2018/0318575 A1* | 11/2018 | Gross | A61N 1/0534 |

FOREIGN PATENT DOCUMENTS

| | | |
|---|---|---|
| WO | 94/05369 | 3/1994 |
| WO | 01/52931 | 7/2001 |
| WO | 01/85027 | 11/2001 |
| WO | 2001/085094 | 11/2001 |
| WO | 2005/011805 A2 | 2/2005 |
| WO | 2006/090397 | 8/2006 |
| WO | 2008/007369 | 1/2008 |
| WO | 2017/006327 | 1/2017 |
| WO | 2017/072769 | 5/2017 |
| WO | 2017/115351 | 7/2017 |
| WO | 2018/051338 | 3/2018 |

OTHER PUBLICATIONS

An Office Action together with the English translation dated Aug. 19, 2020, which issued during the prosecution of Japanese Patent Application No. 2018-521586.

(56) References Cited

OTHER PUBLICATIONS

An Office Action dated Mar. 30, 2020, which issued during the prosecution of U.S. Appl. No. 16/574,772.
An Office Action dated Nov. 29, 2019, which issued during the prosecution of U.S. Appl. No. 15/969,411.
An Office Action dated Jan. 7, 2020, which issued during the prosecution of U.S. Appl. No. 15/618,325.
An Office Action dated Jan. 7, 2020, which issued during the prosecution of European Patent Application No. 16741703.9.
An Office Action dated Jul. 29, 2019, which issued during the prosecution of U.S. Appl. No. 15/618,325.
Sawyer, P N et al. "Measurement of streaming potentials of mammalian blood vessels, aorta and vena cava, in vivo." Biophysical journal vol. 6,5 (1966): 641-51. doi:10.1016/50006-3495(66)86683-3, https://www.ncbi.nlm.nih.gov/pmc/articles/PMC1368020/, viewed on Jul. 22, 2019.
Karran Sep. E et201 al., 1 "The Amyloid cascade hypothesis for AD," Nature Reviews Drug Discovery, vol. 10; 698-712.
De La Tone JC, "Vascular Basis of Alzheimer's Pathogensis," Ann NY Acad Sci. 977:196-215 (Nov. 2002).
Weller RO et al, "Perivascular Drainage of Amyloid-b Peptides from the Brain and Its Failure in Cerebral Amyloid Angiopathy and Alzheimer's Disease," Brain Pathology 18 (Apr. 2008) 253-266.
Brief PubMed search for metal ions in Alzheimers.
An Office Action dated Sep. 27, 2016, which issued during the prosecution of U.S. Appl. No. 14/926,705.
U.S. Appl. No. 62/642,663, filed Mar. 14, 2018.
An International Search Report and a Written Opinion both dated Aug. 7, 2008, which issued during the prosecution of Applicant's PCT/IL2007/000865.
An Office Action dated Mar. 29, 2013, which issued during the prosecution of U.S. Appl. No. 12/373,306.
An Office Action dated Oct. 31, 2011, which issued during the prosecution of U.S. Appl. No. 12/373,306.
An Office Action dated Oct. 1, 2012, which issued during the prosecution of U.S. Appl. No. 12/373,306.
Notice of Allowance dated Jul. 24, 2013, which issued during the prosecution of U.S. Appl. No. 12/373,306.
An Office Action dated Apr. 11, 2013, which issued during the prosecution of U.S. Appl. No. 13/663,757.
Notice of Allowance dated Oct. 28, 2013, which issued during the prosecution of U.S. Appl. No. 13/663,757.
Elixmann IM et al., "In-vitro evaluation of a drainage catheter with integrated bioimpedance electrodes to determine ventricular size," Biomed Tech 2013; 58 (Suppl. 1) Sep. 2013 (2 pages total).
An Office Action dated Aug. 31, 2015, which issued during the prosecution of U.S. Appl. No. 13/872,794.
An Applicant Initiated Summary dated Dec. 14, 2015, which issued during the prosecution of U.S. Appl. No. 13/872,794.
An Office Action dated Feb. 3, 2016, which issued during the prosecution of U.S. Appl. No. 13/872,794.
Notice of Allowance dated Dec. 9, 2016, which issued during the prosecution of U.S. Appl. No. 14/794,739.
An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20, 2016, which issued during the prosecution of Applicant's PCT/IL2016/050728.
An Office Action dated Sep. 21, 2016, which issued during the prosecution of U.S. Appl. No. 14/794,739.
An International Search Report and a Written Opinion both dated Jan. 26, 2017, which issued during the prosecution of Applicant's PCT/IL2016/051161.
Notice of Allowance dated Jul. 14, 2017, which issued during the prosecution of U.S. Appl. No. 13/782,794.
An Office Action dated May 26, 2017, which issued during the prosecution of U.S. Appl. No. 15/453,290.

An International Preliminary Report on Patentability dated Apr. 7, 2009, which issued during the prosecution of Applicant's PCT/IL2007/000865.
Loutzenhiser, "Membrane Potential measurements in renal afferent and efferent arterioles: actions of Angiotensin II", AJP—Renal Physiol Aug. 1, 1997 vol. 273 No. 2 F307-F314.
U.S. Appl. No. 60/830,717, filed Jul. 12, 2006.
Dao-Sheng Liu et al., "Activation of Na+ and K+ Pumping Modes of (Na,K)—ATPase by an Oscillating Electric Field," the Journal of Biological Chemistry, vol. 265. No. 13, May 5, 1990. (pp. 7260-7267).
Robert F. Service.. "Electric fields deliver drugs into tumors." http://news.sciencemaa.ora. Feb. 4, 2015. (5 Pages Total).
Vernengo J, "Injectable Bioadhesive Hydrogels for Nucleus Pulposus Replacement and Repair of the Damaged Intervertebral Disc: A Thesis," Drexel University (Jan. 2007).
Urban JPG et al., "The nucleus of the intervertebral disc from development to degeneration," American Zoologist 40(1): 53-61 (2000).
Cheung KMC et al., "Intervertebral disc regeneration by use of autologous mesenchymal stem cells, an experimental model in rabbits, " Abstract from the SRS 2004 Annual Meeting.
Freemont TJ et al., "Degeneration of intervertebral discs: current understanding of cellular and molecular events, and implications for novel therapies," Expert Reviews in Molecular Biology, Mar. 29, 2001 (Cambridge University Press).
An Office Action dated Sep. 12, 2011, which issued during the prosecution of U.S. Appl. No. 12/373,306.
An Office Action dated Jul. 24, 2017, which issued during the prosecution of U.S. Appl. No. 14/982,187.
An International Search Report and a Written Opinion both dated Mar. 10, 2017, which issued during the prosecution of Applicant's PCT/IL2016/051363.
An Office Action dated Apr. 25, 2018, which issued during the prosecution of U.S. Appl. No. 15/637,330.
U.S. Appl. No. 62/444,939, filed Jan. 11, 2017.
An Office Action dated Jul. 10, 2019, which issued during the prosecution of U.S. Appl. No. 15/864,065.
An International Search Report and a Written Opinion both dated May 23, 2019, which issued during the prosecution of Applicant's PCT/IL2019/050284.
An Office Action dated Mar. 25, 2019, which issued during the prosecution of U.S. Appl. No. 15/742,245.
Borlase NM, "The thalamus in Parkinson's Disease," Department of Psychology, University of Canterbury, 2012.
Fernandes J, "Protein May Prevent Neuron Death in Huntington's Patients, Study Finds," huntingtonsdiseasenews.com, Jan. 19, 2017.
Lee H-J, "Extracellular asynuclein a novel and crucial factor in Lewy body diseases," Nat. Rev. Neurol. 10, 92-98 (Feb. 2014); published online Jan. 28, 2014.
Starr PA et al., "Parkinson's Disease FAQ—Deep Brain Stimulation for Parkinson's Disease," UCSF Apr. 19, 2017.
Perez RG et al., "A Role for Alpha-Synuclein in the Regulation of Dopamine Biosynthesis," The Journal of Neuroscience, Apr. 15, 2002, 22(8):3090-3099.
Breydo L et al., "α-Synuclein misfolding and Parkinson's disease," Biochimica et Biophysica Acta 1822 (2012) 261-285 (Available online Oct. 12, 2011).
Deleidi M et al., "Protein Clearance Mechanisms of Alpha-Synuclein and Amyloid-Beta in Lewy Body Disorders," International Journal of Alzheimer's Disease, vol. 2012.
Xie L et al., "Sleep Drives Metabolite Clearance from the Adult Brain," Science. Oct. 18, 2013; 342(6156).
Valdinocci D et al., "Potential Modes of Intercellular α-Synuclein Transmission," International Journal of Molecular Sciences, Feb. 22, 2017.
U.S. Appl. No. 62/500,747, filed May 3, 2017.
An International Search Report (ISR) and Written Opinion in PCT/IL2020/051022, dated Dec. 20, 2020.
Non-Final Office Action issued in U.S. Appl. No. 16/713,660, dated Nov. 4, 2021.

* cited by examiner

ELECTRICAL SUBSTANCE CLEARANCE FROM THE BRAIN

CROSS-REFERENCE TO RELATED APPLICATIONS

The present application claims the benefit of U.S. Provisional 62/642,663, filed Mar. 14, 2018, which is assigned to the assignee of the present application and incorporated herein by reference. The present application is related to an International Application filed on even date herewith.

FIELD OF THE APPLICATION

The present invention relates generally to treatment and prevention of Alzheimer's disease, Parkinson's disease, and/or cerebral amyloid angiopathy (CAA), and specifically to electrical techniques for treating, preventing, or slowing the progression of Alzheimer's disease, Parkinson's disease, and/or CAA.

BACKGROUND OF THE APPLICATION

Alzheimer's disease is a chronic neurodegenerative disease that causes dementia. Accumulation of substances such as amyloid beta and/or tau protein in the brain is widely believed to contribute to the development of Alzheimer's disease.

Parkinson's disease is a long-term degenerative disorder of the central nervous system that mainly affects the motor system. Deep brain stimulation (DBS) is sometimes used to treat Parkinson's disease and Alzheimer's disease.

U.S. Pat. No. 9,616,221 to Gross, which is assigned to the assignee of the present application and is incorporated herein by reference, describes a method that includes disposing midplane treatment electrodes over a superior sagittal sinus, outside and in electrical contact with a skull of a head of a subject identified as at risk of or suffering from Alzheimer's disease. Lateral treatment electrodes are disposed between 1 and 12 cm of a sagittal midplane of the skull. The subject is treated by electroosmotically driving fluid from a subarachnoid space to the superior sagittal sinus, by activating control circuitry to apply one or more treatment currents between (a) one or more of the midplane treatment electrodes and (b) one or more of the lateral treatment electrodes. Other embodiments are also described.

PCI Publication WO 2017/072769 to Fostick et al., which is assigned to the assignee of the present application and is incorporated herein by reference, describes a system that includes a parenchymal electrode, configured to be implanted in brain parenchyma of a subject identified as at risk of or suffering from a disease; and a cerebrospinal fluid (CST) electrode, configured to be implanted in a CSF-filled space of a brain of the subject, the CSF-filled space selected from the group consisting of: a ventricular system and a subarachnoid space. Control circuitry is configured to drive the parenchymal electrode and the CSF electrode to clear a substance from the brain parenchyma into the CSF-filled space of the brain. Other embodiments are also described.

SUMMARY OF THE APPLICATION

Some embodiments of the present invention provide techniques for treating one or more conditions, such as Alzheimer's disease or Alzheimer's disease and Parkinson's disease, by both deep brain stimulation (DBS) and electrical clearance of a substance, such as amyloid beta and/or metal ions, from brain parenchyma into a cerebrospinal fluid (CSF)-filled space of the brain. At least one electrical lead is used that comprises electrodes used for both the DBS and the electrical clearance of the substance.

There is therefore provided, in accordance with an Inventive Concept 1 of the present invention, apparatus including an electrical brain treatment system, which includes:

a parenchymal electrode, configured to be implanted in direct physical contact with brain tissue of a subject identified as at risk of or suffering from a disease, the brain tissue selected from the group consisting of: brain parenchyma and meninges of the brain;

a cerebrospinal fluid (CSF) electrode, configured to be implanted in a CSF-filled space of a brain of the subject, the CSF-filled space selected from the group consisting of: a ventricular system and a subarachnoid space; and control circuitry, which is electrically coupled to the parenchymal electrode and the CSF electrode, and which is configured to clear a substance from the brain parenchyma into the CSF-filled space of the brain by applying direct current between the parenchymal electrode and the CSF electrode as a series of pulses, with an average amplitude of between 0.25 and 0.5 mA, an average pulse width of between 0.5 and 2 ms, and an average frequency of between 1 and 5 Hz.

Inventive Concept 2. The apparatus according to Inventive Concept 1, wherein the control circuitry is configured to apply the direct current with an average amplitude of between 0.28 and 0.4 mA.

Inventive Concept 3. The apparatus according to Inventive Concept 1, wherein the control circuitry is configured to apply the direct current with an average amplitude of between 0.28 and 0.35 mA.

Inventive Concept 4. The apparatus according to Inventive Concept 1, wherein the control circuitry is configured to apply the direct current with an average pulse width of between 0.8 and 1.2 ins.

Inventive Concept 5. The apparatus according to inventive Concept 1, wherein the control circuitry is configured to apply the direct current with an average frequency of between 1.5 and 3 Hz.

Inventive Concept 6. The apparatus according to Inventive Concept 5, wherein the control circuitry is configured to apply the direct current with an average frequency of between 1.5 and 2.5 Hz.

Inventive Concept 7. The apparatus according to Inventive Concept 1, wherein the control circuitry is configured to apply the direct current with an average amplitude of between 0.28 and 0.35 mA, an average pulse width of between 0.8 and 1.2 ins, and an average frequency of between 1.5 and 2.5 Hz.

Inventive Concept 8. The apparatus according to Inventive Concept I, wherein the control circuitry is configured to apply the direct current as the series of pulses with a duty cycle of between 1% and 30%.

Inventive Concept 9. The apparatus according to Inventive Concept 1, wherein the control circuitry is configured to apply the direct current using an average voltage of less than 1.2 V.

There is further provided, in accordance with an Inventive Concept 10 of the present invention, apparatus including an electrical brain treatment system, which includes:

a parenchymal electrode, configured to be implanted in direct physical contact with brain tissue of a subject identified as at risk of or suffering from a disease, the brain tissue selected from the group consisting of: brain parenchyma and meninges of the brain;

a cerebrospinal fluid (CSF) electrode, configured to be implanted in a CSF-filled space of a brain of the subject, the CSF-filled space selected from the group consisting of: a ventricular system and a subarachnoid space; and control circuitry, which is electrically coupled to the parenchymal electrode and the CSF electrode, and which is configured to clear a substance from the brain parenchyma into the CSF-filled space of the brain by:

applying current between the parenchymal electrode and the CSF electrode as a series of pulses, configuring at least 80% of a charge of the current to have a first polarity and any remainder of the charge of the current to have a second polarity opposite the first polarity, applying the pulses with the first polarity with an average amplitude of between 0.25 and 0.5 mA, an average pulse width of between 0.5 and 2 ms, and an average frequency of between 1 and 5 Hz.

Inventive Concept 11. The apparatus according to Inventive Concept 10, wherein the control circuitry is configured to apply the current as direct current by configuring 100% of the charge of the current to have the first polarity.

Inventive Concept 12. The apparatus according to Inventive Concept 10, wherein the control circuitry is configured to configure less than 100% of the charge of the current to have the first polarity and the remainder of the charge of the current to have the second polarity opposite the first polarity.

Inventive Concept 13. The apparatus according to Inventive Concept 12, wherein the control circuitry is configured to configure at least 90% of the charge of the current to have the first polarity and the remainder of the charge of the current to have the second polarity opposite the first polarity.

Inventive Concept 14. The apparatus according to Inventive Concept 13, wherein the control circuitry is configured to configure at least 95% of the charge of the current to have the first polarity and the remainder of the charge of the current to have the second polarity opposite the first polarity.

Inventive Concept 15. The apparatus according to Inventive Concept 12, wherein the control circuitry is configured to apply the current with the second polarity with an average frequency equal to no more than 20% of the average frequency of the pulses with the first polarity.

Inventive Concept 16. The apparatus according to inventive Concept 12, wherein the control circuitry is configured to apply the current with the first polarity with an average amplitude of between 0.28 and 0.4 mA.

Inventive Concept 17. The apparatus according to Inventive Concept 12, wherein the control circuitry is configured to apply the current with the first polarity with an average amplitude of between 0.28 and 0.35 mA.

Inventive Concept 18. The apparatus according to Inventive Concept 12, wherein the control circuitry is configured to apply the current with the first polarity with an average pulse width of between 0.8 and 1.2 ms.

Inventive Concept 19. The apparatus according to Inventive Concept 12, wherein the control circuitry is configured to apply the current with the first polarity with an average frequency of between 1.5 and 3 Hz.

Inventive Concept 20. The apparatus according to Inventive Concept 19, wherein the control circuitry is configured to apply the current with the first polarity with an average frequency of between 1.5 and 2.5 Hz.

Inventive Concept 21. The apparatus according to Inventive Concept 12, wherein the control circuitry is configured to apply the current with the first polarity with an average amplitude of between 0.28 and 0.35 mA, an average pulse width of between 0.8 and 1.2 ms, and an average frequency of between 1.5 and 2.5 Hz.

Inventive Concept 22. The apparatus according to Inventive Concept 12, wherein the control circuitry is configured to apply the current with the first polarity with as the series of pulses with a duty cycle of between 1% and 30%.

Inventive Concept 23. The apparatus according to Inventive Concept 12, wherein the control circuitry is configured to apply the current with the first polarity using an average voltage of less than 1.2 V.

Inventive Concept 24. The apparatus according to any one of Inventive Concepts 1 or 10, wherein the disease is Alzheimer's disease, and wherein the parenchymal electrode is configured to be implanted in the subject identified as at risk of or suffering from Alzheimer's disease.

Inventive Concept 25. The apparatus according to any one of Inventive Concepts 1 or 10, wherein the disease is cerebral amyloid angiopathy (CAA), and wherein the parenchymal electrode is configured to be implanted in the subject identified as at risk of or suffering from CAA.

Inventive Concept 26. The apparatus according to any one of Inventive Concepts 1 or 10, wherein the CSF-filled space of the brain is the ventricular system, and wherein the CSF electrode is a ventricular electrode, configured to be implanted in the ventricular system.

Inventive Concept 27. The apparatus according to any one of Inventive Concepts 1 or 10, wherein the CSF-filled space of the brain is the subarachnoid space, and wherein the CSF electrode is a subarachnoid electrode, configured to be implanted in the subarachnoid space.

Inventive Concept 28. The apparatus according to any one of Inventive Concepts 1 or 10, wherein the parenchymal electrode is configured to be implanted within the brain parenchyma.

Inventive Concept 29. The apparatus according to Inventive Concept 28, wherein the parenchymal electrode is configured to be implanted in white matter of the brain.

Inventive Concept 30. The apparatus according to any one of Inventive Concepts 1 or 10, wherein the parenchymal electrode is configured to be implanted in direct physical contact with the meninges of the brain.

Inventive Concept 31. The apparatus according to any one of Inventive Concepts 1 or 10, wherein the substance includes amyloid beta, and wherein the control circuitry is configured to drive the parenchymal electrode and the CSF electrode to clear the amyloid beta from the brain parenchyma into the CSF-filled space of the brain.

Inventive Concept 32. The apparatus according to any one of Inventive Concepts 1 or 10, wherein the substance includes metal ions, and wherein the control circuitry is configured to drive the parenchymal electrode and the CSF electrode to clear the metal ions from the brain parenchyma into the CSF-filled space of the brain.

Inventive Concept 33. The apparatus according to any one of Inventive Concepts 1 or 10, wherein the substance includes tau protein, and wherein the control circuitry is configured to drive the parenchymal electrode and the CSF electrode to clear the tau protein from the brain parenchyma into the CSF-filled space of the brain.

Inventive Concept 34. The apparatus according to any one of Inventive Concepts 1 or 10, wherein the control circuitry is configured to drive the parenchymal electrode and the CSF electrode to clear the substance by applying non-excitatory current between the parenchymal electrode and the CSF electrode.

There is still further provided, in accordance with an Inventive Concept 35 of the present invention, a method including:
- implanting a parenchymal electrode of an electrical brain treatment system in direct physical contact with brain tissue of a subject identified as at risk of or suffering from a disease, the brain tissue selected from the group consisting of: brain parenchyma and meninges of the brain;
- implanting a cerebrospinal fluid (CSF) electrode of the electrical brain treatment system in a CSF-filled space of a brain of the subject, the CSF-filled space selected from the group consisting of a ventricular system and a subarachnoid space; and
- activating control circuitry, which is electrically coupled to the parenchymal electrode and the CSF electrode, to clear a substance from the brain parenchyma into the CSF-filled space of the brain by applying direct current between the parenchymal electrode and the CSF electrode as a series of pulses, with an average amplitude of between 0.25 and 0.5 mA, an average pulse width of between 0.5 and 2 ms, and an average frequency of between 1 and 5 Hz.

There is additionally provided, in accordance with an Inventive Concept 36 of the present invention, a method including:
- implanting a parenchymal electrode of an electrical brain treatment system in direct physical contact with brain tissue of a subject identified as at risk of or suffering from a disease, the brain tissue selected from the group consisting of: brain parenchyma and meninges of the brain;
- implanting a cerebrospinal fluid (CSF) electrode of the electrical brain treatment system in a CSF-filled space of a brain of the subject, the CSF-filled space selected from the group consisting of: a ventricular system and a subarachnoid space; and
- activating control circuitry, which is electrically coupled to the parenchymal electrode and the CSF electrode, to clear a substance from the brain parenchyma into the CSF-filled space of the brain by:
  - applying current between the parenchymal electrode and the CSF electrode as a series of pulses,
  - configuring at least 80% of a charge of the current to have a first polarity and any remainder of the charge of the current to have a second polarity opposite the first polarity,
  - applying the pulses with the first polarity with an average amplitude of between 0.25 and 0.5 mA, an average pulse width of between 0.5 and 2 ms, and an average frequency of between 1 and 5 Hz.

Inventive Concept 37. The method according to Inventive Concept 36, wherein activating the control circuitry includes activating the control circuitry to apply the current as direct current by configuring 100% of the charge of the current to have the first polarity.

Inventive Concept 38. The method according to Inventive Concept 36, wherein activating the control circuitry includes activating the control circuitry to configure less than 100% of the charge of the current to have the first polarity and the remainder of the charge of the current to have the second polarity opposite the first polarity.

Inventive Concept 39. The method according to Inventive Concept 38, wherein activating the control circuitry includes activating the control circuitry to configure at least 90% of the charge of the current to have the first polarity and the remainder of the charge of the current to have the second polarity opposite the first polarity.

Inventive Concept 40. The method according to Inventive Concept 39, wherein activating the control circuitry includes activating the control circuitry to configure at least 95% of the charge of the current to have the first polarity and the remainder of the charge of the current to have the second polarity opposite the first polarity.

There is yet additionally provided, in accordance with an inventive Concept 41 of the present invention, apparatus including an electrical brain treatment system, which includes:
- a parenchymal electrode, configured to be implanted in direct physical contact with brain tissue of a subject identified as at risk of or suffering from a disease, the brain tissue selected from the group consisting of: brain parenchyma and meninges of the brain;
- a cerebrospinal fluid (CSF) electrode, configured to be implanted in a CSF-filled space of a brain of the subject, the CSF-filled space selected from the group consisting of: a ventricular system and a subarachnoid space; and
- control circuitry, which is electrically coupled to the parenchymal electrode and the CSF electrode, and which is configured to clear a substance from the brain parenchyma into the CSF-filled space of the brain by:
  - applying current between the parenchymal electrode and the CSF electrode as a series of pulses,
  - configuring at least 80% of a charge of the current to have a first polarity and any remainder of the charge of the current to have a second polarity opposite the first polarity,
  - applying the pulses with the first polarity with an average amplitude of between 0.25 and 0.5 mA, an average pulse width of between 0.5 and 2 ms, and an average frequency of between 1 and 5 Hz.

There is also provided, in accordance with an Inventive Concept 42 of the present invention, apparatus including an electrical brain treatment system, which includes:
- a parenchymal electrode, configured to be implanted in direct physical contact with brain tissue of a subject identified as at risk of or suffering from a disease, the brain tissue selected from the group consisting of: brain parenchyma and meninges of the brain;
- a cerebrospinal fluid (CSF) electrode, configured to be implanted in a CSF-filled space of a brain of the subject, the CSF-filled space selected from the group consisting of: a ventricular system and a subarachnoid space; and
- control circuitry, which is electrically coupled to the parenchymal electrode and the CSF electrode, and which is configured to clear a substance from the brain parenchyma into the CSF-filled space of the brain by:
  - applying current between the parenchymal electrode and the CSF electrode as a series of pulses,
  - configuring at least 80% but less than 100% of a charge of the current to have a first polarity and any remainder of the charge of the current to have a second polarity opposite the first polarity.

Inventive Concept 43. The apparatus according to Inventive Concept 42, wherein the control circuitry is configured to configure at least 90% of the charge of the current to have the first polarity and the remainder of the charge of the current to have the second polarity opposite the first polarity.

Inventive Concept 44. The apparatus according to Inventive Concept 43, wherein the control circuitry is configured to configure at least 9.5% of the charge of the current to have the first polarity and the remainder of the charge of the current to have the second polarity opposite the first polarity.

Inventive Concept 45. The apparatus according to Inventive Concept 42, wherein the control circuitry is configured to apply the current with the second polarity with an average frequency equal to no more than 20% of the average frequency of the pulses with the first polarity.

Inventive Concept 46. The apparatus according to Inventive Concept 42, wherein the control circuitry is configured to apply the pulses with the first polarity with an average amplitude of between 0.25 and 0.5 mA.

Inventive Concept 47. The apparatus according to Inventive Concept 42, wherein the control circuitry is configured to apply the pulses with the first polarity with an average pulse width of between 0.5 and 2 ms.

Inventive Concept 48. The apparatus according to Inventive Concept 42, wherein the control circuitry is configured to apply the pulses with the first polarity with an average frequency of between 1 and 5 Hz.

Inventive Concept 49. The apparatus according to Inventive Concept 42, wherein the disease is Alzheimer's disease, and wherein the parenchymal electrode is configured to be implanted in the subject identified as at risk of or suffering from Alzheimer's disease.

Inventive Concept 50. The apparatus according to Inventive Concept 42, wherein the disease is cerebral amyloid angiopathy (CAA), and wherein the parenchymal electrode is configured to be implanted in the subject identified as at risk of or suffering from CAA.

Inventive Concept 51. The apparatus according to Inventive Concept 42, wherein the CSF-filled space of the brain is the ventricular system, and wherein the CSF electrode is a ventricular electrode, configured to be implanted in the ventricular system.

Inventive Concept 52. The apparatus according to inventive Concept 42, wherein the CSF-filled space of the brain is the subarachnoid space, and wherein the CSF electrode is a subarachnoid electrode, configured to be implanted in the subarachnoid space.

Inventive Concept 53. The apparatus according to Inventive Concept 42, wherein the parenchymal electrode is configured to be implanted within the brain parenchyma.

Inventive Concept 54. The apparatus according to Inventive Concept 53, wherein the parenchymal electrode is configured to be implanted in white matter of the brain.

Inventive Concept 55. The apparatus according to Inventive Concept 42, wherein the parenchymal electrode is configured to be implanted in direct physical contact with the meninges of the brain.

Inventive Concept 56. The apparatus according to Inventive Concept 42, wherein the substance includes amyloid beta, and wherein the control circuitry is configured to drive the parenchymal electrode and the CSF electrode to clear the amyloid beta from the brain parenchyma into the CSF-filled space of the brain.

Inventive Concept 57. The apparatus according to Inventive Concept 42, wherein the substance includes metal ions, and wherein the control circuitry is configured to drive the parenchymal electrode and the CSF electrode to clear the metal ions from the brain parenchyma into the CSF-filled space of the brain.

Inventive Concept 58. The apparatus according to Inventive Concept 42, wherein the substance includes tau protein, and wherein the control circuitry is configured to drive the parenchymal electrode and the CSF electrode to clear the tau protein from the brain parenchyma into the CSF-filled space of the brain.

Inventive Concept 59. The apparatus according to Inventive Concept 42, wherein the control circuitry is configured to drive the parenchymal electrode and the CSF electrode to clear the substance by applying non-excitatory current between the parenchymal electrode and the CSF electrode.

There is further provided, in accordance with an Inventive Concept 60 of the present invention, apparatus including an electrical brain treatment system, which includes:
  a parenchymal electrode, configured to be implanted in direct physical contact with brain tissue of a subject identified as at risk of or suffering from a disease, the brain tissue selected from the group consisting of: brain parenchyma and meninges of the brain;
  a cerebrospinal fluid (CST) electrode, configured to be implanted in a CSF-filled space of a brain of the subject, the CSF-filled space selected from the group consisting of: a ventricular system and a subarachnoid space; and
  control circuitry, which is electrically coupled to the parenchymal electrode and the CSF electrode, and which is configured to:
    clear a substance from the brain parenchyma into the CSF-filled space of the brain, by applying current with a first polarity between the parenchymal electrode and the CSF electrode, and
    release at least a portion of the substance that may build up on the CSF electrode from the CSF electrode into the CSF of the CSF-filled space, by applying the current with a second polarity between the parenchymal electrode and the CSF electrode, the second polarity opposite the first polarity.

Inventive Concept 61. The apparatus according to Inventive Concept 60, wherein the control circuitry is configured to apply the current with the second polarity to return to the brain parenchyma no more than 10% by weight of the substance released from the CSF electrode.

Inventive Concept 62. The apparatus according to Inventive Concept 61, wherein the control circuitry is configured to apply the current with the second polarity to return to the brain parenchyma no more than 1% by weight of the substance released from the CSF electrode.

Inventive Concept 63. The apparatus according to Inventive Concept 60, wherein the control circuitry is configured to configure at least 80% but less than 100% of a charge of the current to have the first polarity and the remainder of the charge of the current to have the second polarity opposite the first polarity.

Inventive Concept 64. The apparatus according to Inventive Concept 63, wherein the control circuitry is configured to configure at least 90% of the charge of the current to have the first polarity and the remainder of the charge of the current to have the second polarity opposite the first polarity.

Inventive Concept 65. The apparatus according to inventive Concept 64, wherein the control circuitry is configured to configure at least 95% of the charge of the current to have the first polarity and the remainder of the charge of the current to have the second polarity opposite the first polarity.

Inventive Concept 66. The apparatus according to Inventive Concept 60, wherein the control circuitry is configured to apply the current as a series of pulses.

Inventive Concept 67. The apparatus according to Inventive Concept 66, wherein the control circuitry is configured to apply the pulses with the first polarity with an average amplitude of between 0.25 and 0.5 mA.

Inventive Concept 68. The apparatus according to Inventive Concept 66, wherein the control circuitry is configured to apply the pulses with the first polarity with an average pulse width of between 0.5 and 2 ms.

Inventive Concept 69. The apparatus according to Inventive Concept 66, wherein the control circuitry is configured to apply the pulses with the first polarity with an average frequency of between 1 and 5 Hz.

Inventive Concept 70. The apparatus according to Inventive Concept 60, wherein the disease is Alzheimer's disease, and wherein the parenchymal electrode is configured to be implanted in the subject identified as at risk of or suffering from Alzheimer's disease.

Inventive Concept 71. The apparatus according to Inventive Concept 60, wherein the disease is cerebral amyloid angiopathy (CAA), and wherein the parenchymal electrode is configured to be implanted in the subject identified as at risk of or suffering from CAA.

Inventive Concept 72. The apparatus according to Inventive Concept 60, wherein the CSF-filled space of the brain is the ventricular system, and wherein the CSF electrode is a ventricular electrode, configured to be implanted in the ventricular system.

Inventive Concept 73. The apparatus according to Inventive Concept 60, wherein the CSF-filled space of the brain is the subarachnoid space, and wherein the CSF electrode is a subarachnoid electrode, configured to be implanted in the subarachnoid space.

Inventive Concept 74. The apparatus according to Inventive Concept 60, wherein the parenchymal electrode is configured to be implanted within the brain parenchyma.

Inventive Concept 75. The apparatus according to Inventive Concept 74, wherein the parenchymal electrode is configured to be implanted in white matter of the brain.

Inventive Concept 76. The apparatus according to Inventive Concept 60, wherein the parenchymal electrode is configured to be implanted in direct physical contact with the meninges of the brain.

Inventive Concept 77. The apparatus according to Inventive Concept 60, wherein the substance includes amyloid beta, and wherein the control circuitry is configured to drive the parenchymal electrode and the CSF electrode to clear the amyloid beta from the brain parenchyma into the CSF-filled space of the brain.

Inventive Concept 78. The apparatus according to Inventive Concept 60, wherein the substance includes metal ions, and wherein the control circuitry is configured to drive the parenchymal electrode and the CSF electrode to clear the metal ions from the brain parenchyma into the CSF-filled space of the brain.

Inventive Concept 79. The apparatus according to Inventive Concept 60, wherein the substance includes tau protein, and wherein the control circuitry is configured to drive the parenchymal electrode and the CSF electrode to clear the tau protein from the brain parenchyma into the CSF-filled space of the brain.

Inventive Concept 80. The apparatus according to Inventive Concept 60, wherein the control circuitry is configured to drive the parenchymal electrode and the CSF electrode to clear the substance by applying non-excitatory current between the parenchymal electrode and the CSF electrode.

There is still further provided, in accordance with an Inventive Concept 81 of the present invention, a method including:
 implanting a parenchymal electrode of an electrical brain treatment system in direct physical contact with brain tissue of a subject identified as at risk of or suffering from a disease, the brain tissue selected from the group consisting of: brain parenchyma and meninges of the brain;
 implanting a cerebrospinal fluid (CSF) electrode of the electrical brain treatment system in a CSF-tilled space of a brain of the subject, the CSF-tilled space selected from the group consisting of: a ventricular system and a subarachnoid space; and
 activating control circuitry, which is electrically coupled to the parenchymal electrode and the CSF electrode, to:
  clear a substance from the brain parenchyma into the CSF-filled space of the brain, by applying current with a first polarity between the parenchymal electrode and the CSF electrode, and
  release any of the substance that may build up on the CSF electrode from the CSF electrode into the CSF of the CSF-filled space. by applying the current with a second polarity between the parenchymal electrode and the CSF electrode, the second polarity opposite the first polarity.

Inventive Concept 82. The method according to Inventive Concept 81, wherein activating the control circuitry includes activating the control circuitry to apply the current with the second polarity to return to the brain parenchyma no more than 10% by weight of the substance released from the CSF electrode.

There is additionally provided, in accordance with an Inventive Concept 83 of the present invention, apparatus including an electrical brain treatment system, which includes:
 (a) an electrical lead, which is configured to be implanted in a brain of a subject identified as at risk of or suffering from at least one disease, and which includes:
  an elongate support structure;
  deep brain stimulation (DBS) electrodes, fixed to the elongate support structure, and configured to be implanted in a deep brain structure; and
  a parenchymal electrode, fixed to the elongate support structure at least 3 cm from a closest one of the DBS electrodes, and configured to be implanted in direct physical contact with brain tissue selected from the group consisting of brain parenchyma and meninges of the brain;
 (b) a cerebrospinal fluid (CSF) electrode, configured to be implanted in a CST-filled space of the brain, the CSF-filled space selected from the group consisting of a ventricular system and a subarachnoid space; and
 (c) control circuitry, which is electrically coupled to the electrical lead, and which is configured to (i) drive the DBS electrodes to apply DBS to the deep brain structure, and (ii) drive the parenchymal electrode and the CSF electrode to clear a substance from the brain parenchyma into the CSF-filled space.

Inventive Concept 84. The apparatus according to Inventive Concept 83, wherein the at least one disease includes Alzheimer's disease, and wherein the electrical lead is configured to be implanted in the brain of the subject identified as at risk of or suffering from Alzheimer's disease.

Inventive Concept 85. The apparatus according to Inventive Concept 83, wherein the at least one disease includes Alzheimer's disease and Parkinson's disease, and wherein the electrical lead is configured to be implanted in the brain of the subject identified as at risk of or suffering from Alzheimer's disease and Parkinson's disease.

Inventive Concept 86. The apparatus according to Inventive Concept 83, wherein the at least one disease includes cerebral amyloid angiopathy (CAA), and wherein the electrical lead is configured to be implanted in the brain of the subject identified as at risk of or suffering from CAA.

Inventive Concept 87. The apparatus according to Inventive Concept 83, wherein the elongate support structure has a length of between 3 and 25 cm.

Inventive Concept 88. The apparatus according to Inventive Concept 83, wherein the deep brain structure is selected from the group consisting of: a thalamus, a subthalamic nucleus (STN), a globus pallidus (GPi), an intermediate thalamus (VIM) in the thalamus, caudal zona incerta, and pallidofugal fibers medial to the STN.

Inventive Concept 89. The apparatus according to Inventive Concept 83, wherein the deep brain structure is selected from the group consisting of: a hippocampus and a fornix.

Inventive Concept 90. The apparatus according to Inventive Concept 83, wherein the CSF-filled space of the brain is the ventricular system, and wherein the CSF electrode is a ventricular electrode, configured to be implanted in the ventricular system.

Inventive Concept 91. The apparatus according to inventive Concept 83, wherein the CSF-filled space of the brain is the subarachnoid space, and wherein the CSF electrode is a subarachnoid electrode, configured to be implanted in the subarachnoid space.

Inventive Concept 92. The apparatus according to Inventive Concept 83, wherein the parenchymal electrode is configured to be implanted within the brain parenchyma.

Inventive Concept 93. The apparatus according to Inventive Concept 92, wherein the parenchymal electrode is configured to be implanted in white matter of the brain.

Inventive Concept 94. The apparatus according to Inventive Concept 92, wherein the parenchymal electrode is configured to be implanted a cerebral cortex of the brain.

Inventive Concept 95. The apparatus according to Inventive Concept 83, wherein the parenchymal electrode is configured to be implanted in direct physical contact with the meninges of the brain.

Inventive Concept 96. The apparatus according to Inventive Concept 83, wherein the substance includes amyloid beta, and wherein the control circuitry is configured to drive the parenchymal electrode and the CSF electrode to clear the amyloid beta from the brain parenchyma into the CSF-filled space of the brain.

Inventive Concept 97. The apparatus according to Inventive Concept 83, wherein the substance includes metal ions, and wherein the control circuitry is configured to drive the parenchymal electrode and the CSF electrode to clear the metal ions from the brain parenchyma into the CSF-filled space of the brain.

Inventive Concept 98. The apparatus according to Inventive Concept 83, wherein the substance includes tau protein, and wherein the control circuitry is configured to drive the parenchymal electrode and the CSF electrode to clear the tau protein from the brain parenchyma into the CSF-filled space of the brain.

Inventive Concept 99. The apparatus according to Inventive Concept 83, wherein the control circuitry is configured to drive the parenchymal electrode and the CSF electrode to clear the substance by applying non-excitatory current between the parenchymal electrode and the CSF electrode.

Inventive Concept 100, The apparatus according to any one of Inventive Concepts 83-99, wherein the control circuitry is configured to drive the parenchymal electrode and the CSF electrode to clear the substance by applying direct current between the parenchymal electrode and the CSF electrode.

Inventive Concept 101. The apparatus according to Inventive Concept 100, wherein the control circuitry is configured to drive the parenchymal electrode and the CSF electrode to apply the direct current as a series of pulses.

Inventive Concept 102. The apparatus according to Inventive Concept 101, wherein the control circuitry is configured to apply the direct pulses with an average amplitude of between 0.25 and 0.5 mA, an average pulse width of between 0.5 and 2 ms, and an average frequency of between 1 and 5 Hz.

Inventive Concept 103. The apparatus according to Inventive Concept 100, wherein the control circuitry is configured to apply the direct current using an average voltage of less than 1.2 V.

Inventive Concept 104. The apparatus according to any one of Inventive Concepts 83-99, wherein the control circuitry is configured to drive the parenchymal electrode and the CSF electrode to clear the substance by applying current between the parenchymal electrode and the CSF electrode, and configuring at least 80% but less than 100% of a charge of the current to have a first polarity and the remainder of the charge of the current to have a second polarity opposite the first polarity.

Inventive Concept 105. The apparatus according to Inventive Concept 104, wherein the control circuitry is configured to drive the parenchymal electrode and the CSF electrode to apply the current as a series of pulses.

Inventive Concept 106. The apparatus according to Inventive Concept 105, wherein the control circuitry is configured to apply the pulses with the first polarity with an average amplitude of between 0.25 and 0.5 mA, an average pulse width of between 0.5 and 2 ms, and an average frequency of between 1 and 5 Hz.

Inventive Concept 107. The apparatus according to Inventive Concept 104, wherein the control circuitry is configured to apply the current using an average voltage of less than 1.2 V.

Inventive Concept 108. The apparatus according to any one of Inventive Concepts 83-99, wherein the control circuitry is configured to drive the DBS electrodes to apply the DBS as a series of pulses having a frequency of between 100 and 150 Hz.

Inventive Concept 109. The apparatus according to any one of Inventive Concepts 83-99, wherein the CSF electrode is fixed to the elongate support structure.

Inventive Concept 110. The apparatus according to Inventive Concept 109, wherein the CSF electrode is fixed to the elongate support structure longitudinally between the parenchymal electrode and the DBS electrodes.

Inventive Concept 111, The apparatus according to any one of Inventive Concepts 83-99,
wherein the electrical lead is a first electrical lead, and the elongate support structure is a first elongate support structure,
wherein the electrical brain treatment system further includes a second electrical lead, which includes a second elongate support structure,
wherein the CSF electrode is fixed to the second elongate support structure, and
wherein the control circuitry is electrically coupled to the first and the second electrical leads.

Inventive Concept 112. The apparatus according to any one of inventive Concepts 83-99,
wherein the DBS electrodes and the parenchymal electrode are electrically coupled to the control circuitry via a proximal end of the elongate support structure, wherein the DBS electrodes are fixed to the elongate support structure near a distal end of the elongate support structure, wherein the electrical lead further includes a supplemental clearance electrode, which is fixed to the elongate support structure no more proximally than a proximal-most one of the DBS electrodes, and wherein the control circuitry is configured to drive the supplemental clearance electrode and the CSF electrode to clear the substance from the brain parenchyma into the CSF-filled space.

Inventive Concept 113. The apparatus according to any one of Inventive Concepts 83-99, Wherein the control circuitry is configured to drive the CSF electrode and one or more of the DBS electrodes to clear the substance from the brain parenchyma into the CSF-filled space.

There is yet additionally provided, in accordance with an Inventive Concept 114 of the present invention, apparatus including an electrical brain treatment system, which includes:

(a) a first electrical lead, which is configured to be implanted in a brain of a subject identified as at risk of or suffering from at least one disease, and which includes:
  a first elongate support structure;
  deep brain stimulation (DBS) electrodes, fixed to the first elongate support structure, and configured to be implanted in a deep brain structure; and
  a cerebrospinal fluid (CSF) electrode, fixed to the first elongate support structure, and configured to be implanted in a CSF-filled space of the brain, the CSF-filled space selected from the group consisting of: a ventricular system and a subarachnoid space;

(b) a second electrical lead, which is configured to be implanted in the brain, and which includes:
  a second elongate support structure; and
  a parenchymal electrode, fixed to the second elongate support structure, and configured to be implanted in direct physical contact with brain tissue selected from the group consisting of: brain parenchyma and meninges of the brain; and (c) control circuitry, which is electrically coupled to the first and the second electrical leads, and which is configured to (i) drive the DBS electrodes to apply deep brain stimulation (DBS) to the deep brain structure, and (ii) drive the parenchymal electrode and the CSF electrode to clear a substance from the brain parenchyma into the CSF-filled space.

Inventive Concept 115. The apparatus according to Inventive Concept 114, wherein the DBS electrodes and the CSF electrode are electrically coupled to the control circuitry via a proximal end of the first elongate support structure, wherein the DBS electrodes are fixed to the first elongate support structure near a distal end of the first elongate support structure, and wherein the CSF electrode is fixed to the first elongate support structure proximal to a proximal-most one of the DBS electrodes.

Inventive Concept 116. The apparatus according to Inventive Concept 114, wherein the first elongate support structure has a length of between 3 and 25 cm.

Inventive Concept 117. The apparatus according to Inventive Concept 114, wherein the deep brain structure is selected from the group consisting of: a thalamus, a subthalamic nucleus (STN), a globus pallidus (GPi), an intermediate thalamus (VIM) in the thalamus, caudal zona incerta, and pallidofugal fibers medial to the SIN.

Inventive Concept 118. The apparatus according to Inventive Concept 114, wherein the deep brain structure is selected from the group consisting of: a hippocampus and a fornix.

Inventive Concept 119. The apparatus according to Inventive Concept 114, wherein the at least one disease includes Alzheimer's disease, and wherein the electrical lead is configured to be implanted in the brain of the subject identified as at risk of or suffering from Alzheimer's disease.

Inventive Concept 120. The apparatus according to Inventive Concept 114, wherein the at least one disease includes Alzheimer's disease and Parkinson's disease, and wherein the electrical lead is configured to be implanted in the brain of the subject identified as at risk of or suffering from Alzheimer's disease and Parkinson's disease.

Inventive Concept 121. The apparatus according to Inventive Concept 114, wherein the at least one disease includes cerebral amyloid angiopathy (CAA), and wherein the electrical lead is configured to be implanted in the brain of the subject identified as at risk of or suffering from CAA.

Inventive Concept 122. The apparatus according to Inventive Concept 114, wherein the CSF-filled space of the brain is the ventricular system, and wherein the CSF electrode is a ventricular electrode, configured to be implanted in the ventricular system.

Inventive Concept 123. The apparatus according to Inventive Concept 114, wherein the CSF-filled space of the brain is the subarachnoid space, and wherein the CSF electrode is a subarachnoid electrode, configured to be implanted in the subarachnoid space.

Inventive Concept 124. The apparatus according to Inventive Concept 114, wherein the substance includes amyloid beta, and wherein the control circuitry is configured to drive the parenchymal electrode and the CSF electrode to clear the amyloid beta from the brain parenchyma into the CSF-filled space of the brain.

Inventive Concept 125. The apparatus according to Inventive Concept 114, wherein the substance includes metal ions, and wherein the control circuitry is configured to drive the parenchymal electrode and the CSF electrode to clear the metal ions from the brain parenchyma into the CSF-filled space of the brain.

Inventive Concept 126. The apparatus according to Inventive Concept 114, wherein the substance includes tau protein, and wherein the control circuitry is configured to drive the parenchymal electrode and the CSF electrode to clear the tau protein from the brain parenchyma into the CSF-filled space of the brain.

Inventive Concept 127. The apparatus according to Inventive Concept 114, wherein the control circuitry is configured to drive the parenchymal electrode and the CSF electrode to clear the substance by applying non-excitatory current between the parenchymal electrode and the CSF electrode.

Inventive Concept 128. The apparatus according to any one of Inventive Concepts 114-127, wherein the control circuitry is configured to drive the parenchymal electrode and the CSF electrode to clear the substance by applying direct current between the parenchymal electrode and the CSF electrode.

Inventive Concept 129. The apparatus according to Inventive Concept 128, wherein the control circuitry is configured to drive the parenchymal electrode and the CSF electrode to apply the direct current as a series of pulses.

Inventive Concept 130. The apparatus according to Inventive Concept 129, wherein the control circuitry is configured to apply the direct pulses with an average amplitude of between 0.25 and 0.5 mA, an average pulse width of between 0.5 and 2 ms, and an average frequency of between 1 and 5 Hz.

Inventive Concept 131. The apparatus according to Inventive Concept 128, wherein the control circuitry is configured to apply the direct current using an average voltage of less than 1.2 V.

Inventive Concept 132. The apparatus according to any one of Inventive Concepts 114-127, wherein the control circuitry is configured to drive the parenchymal electrode and the CSF electrode to clear the substance by applying current between the parenchymal electrode and the CSF electrode, and configuring at least 80% but less than 100% of a charge of the current to have a first polarity and the remainder of the charge of the current to have a second polarity opposite the first polarity.

Inventive Concept 133. The apparatus according to Inventive Concept 132, wherein the control circuitry is configured to drive the parenchymal electrode and the CSF electrode to apply the current as a series of pulses.

Inventive Concept 134. The apparatus according to Inventive Concept 133, wherein the control circuitry is configured to apply the pulses with the first polarity with an average amplitude of between 0.25 and 0.5 mA, an average pulse width of between 0.5 and 2 ins, and an average frequency of between 1 and 5 Hz.

Inventive Concept 135. The apparatus according to Inventive Concept 132, wherein the control circuitry is configured to apply the current using an average voltage of less than 1.2 V.

Inventive Concept 136. The apparatus according to any one of Inventive Concepts 114-127, wherein the control circuitry is configured to drive the DBS electrodes to apply the DBS as a series of pulses having a frequency of between 100 and 150 Hz.

There is also provided, in accordance with an Inventive Concept 137 of the present invention, apparatus including an electrical brain treatment system, which includes:
(a) an electrical lead, which is configured to be implanted in a brain of a subject identified as at risk of or suffering from at least one disease, and which includes:
an elongate support structure; and
brain tissue electrodes, fixed to the elongate support structure, and configured to be implanted in a deep brain structure;
(b) a cerebrospinal fluid (CSF) electrode, configured to be implanted in a CSF-filled space of the brain, the CSF-filled space selected from the group consisting of a ventricular system and a subarachnoid space; and
(c) control circuitry, which is electrically coupled to the electrical lead, and which is configured to (i) drive one or more of the brain tissue electrodes to apply deep brain stimulation (DBS) to the deep brain structure, and (ii) drive the CSF electrode and one or more of the brain tissue electrodes to clear a substance from brain parenchyma into the CSF-filled space.

Inventive Concept 138. The apparatus according to Inventive Concept 137, wherein the control circuitry is configured to simultaneously (a) drive the one or more of the brain tissue electrodes to apply the DBS to the deep brain structure, and (b) drive the CSF electrode and the one or more of the brain tissue electrodes to clear the substance from the brain parenchyma into the CSF-filled space.

Inventive Concept 139. The apparatus according to Inventive Concept 137, wherein the control circuitry is configured to alternatingly (a) drive the one or more of the brain tissue electrodes to the DBS to the deep brain structure, and (b) drive the CSF electrode and the one or more of the brain tissue electrodes to clear the substance from the brain parenchyma into the CSF-filled space.

Inventive Concept 140. The apparatus according to Inventive Concept 137, wherein the elongate support structure has a length of between 3 and 25 cm.

Inventive Concept 141. The apparatus according to Inventive Concept 137, wherein the CSF electrode is fixed to the elongate support structure.

Inventive Concept 142. The apparatus according to Inventive Concept 137, wherein the electrical lead is a first electrical lead, and the elongate support structure is a first elongate support structure,
wherein the electrical brain treatment system further includes a second electrical lead, which includes a second elongate support structure,
wherein the CSF electrode is fixed to the second elongate support structure, and
wherein the control circuitry is electrically coupled to the first and the second electrical leads.

Inventive Concept 143. The apparatus according to Inventive Concept 137, wherein the control circuitry is configured to drive the CSF electrode and the one or more of the brain tissue electrodes to clear the substance by applying direct current between the CSF electrode and the one or more of the brain tissue electrodes.

Inventive Concept 144. The apparatus according to Inventive Concept 143, wherein the control circuitry is configured to drive the CSF electrode and the one or more of the brain tissue electrodes to apply the direct current as a series of pulses.

Inventive Concept 145. The apparatus according to Inventive Concept 144, wherein the control circuitry is configured to apply the direct pulses with an average amplitude of between 0.25 and 0.5 mA, an average pulse width of between 0.5 and 2 ms, and an average frequency of between 1 and 5 Hz.

Inventive Concept 146. The apparatus according to Inventive Concept 143, wherein the control circuitry is configured to apply the direct current using an average voltage of less than 1.2 V.

Inventive Concept 147. The apparatus according to Inventive Concept 137, wherein the control circuitry is configured to drive the CSF electrode and the one or more of the brain tissue electrodes to clear the substance by applying current between the CSF electrode and the one or more of the brain tissue electrodes, and configuring at least 80% but less than 100% of a charge of the current to have a first polarity and the remainder of the charge of the current to have a second polarity opposite the first polarity.

Inventive Concept 148. The apparatus according to Inventive Concept 147, wherein the control circuitry is configured to drive the CSF electrode and the one or more of the brain tissue electrodes to apply the current as a series of pulses.

Inventive Concept 149. The apparatus according to Inventive Concept 148, wherein the control circuitry is configured to apply the pulses with the first polarity with an average amplitude of between 0.25 and 0.5 mA, an average pulse width of between 0.5 and 2 ms, and an average frequency of between 1 and 5 Hz.

Inventive Concept 150. The apparatus according to Inventive Concept 147, wherein the control circuitry is configured to apply the current using an average voltage of less than 1.2 V.

Inventive Concept 151. The apparatus according to Inventive Concept 137, wherein the control circuitry is configured to drive the DBS electrodes to apply the DBS as a series of pulses having a frequency of between 100 and 150 Hz.

Inventive Concept 152. The apparatus according to Inventive Concept 137, wherein the deep brain structure is selected from the group consisting of: a thalamus, a subthalamic nucleus (STN), a globus pallidus (GPi), an intermediate thalamus (VIM) in the thalamus, caudal zona incerta, and pallidofugal fibers medial to the STN.

Inventive Concept 153. The apparatus according to Inventive Concept 137, wherein the deep brain structure is selected from the group consisting of: a hippocampus and a fornix.

Inventive Concept 154. The apparatus according to Inventive Concept 137, wherein the at least one disease includes Alzheimer's disease, and wherein the electrical lead is configured to be implanted in the brain of the subject identified as at risk of or suffering from Alzheimer's disease.

Inventive Concept 155. The apparatus according to Inventive Concept 137, wherein the at least one disease includes Alzheimer's disease and Parkinson's disease, and wherein the electrical lead is configured to be implanted in the brain of the subject identified as at risk of or suffering from Alzheimer's disease and Parkinson's disease.

Inventive Concept 156. The apparatus according to Inventive Concept 137, wherein the at least one disease includes cerebral amyloid angiopathy (CAA), and wherein the electrical lead is configured to be implanted in the brain of the subject identified as at risk of or suffering from CAA.

Inventive Concept 157. The apparatus according to inventive Concept 137, wherein the CSF-filled space of the brain is the ventricular system, and wherein the CSF electrode is a ventricular electrode, configured to be implanted in the ventricular system.

Inventive Concept 158. The apparatus according to Inventive Concept 137, wherein the CSF-filled space of the brain is the subarachnoid space, and wherein the CSF electrode is a subarachnoid electrode, configured to be implanted in the subarachnoid space.

Inventive Concept 159. The apparatus according to Inventive Concept 137, wherein the substance includes amyloid beta, and wherein the control circuitry is configured to drive the CSF electrode and the one or more of the brain tissue electrodes to clear the amyloid beta from the brain parenchyma into the CSF-filled space of the brain.

Inventive Concept 160. The apparatus according to Inventive Concept 137, wherein the substance includes metal ions, and wherein the control circuitry is configured to drive the CSF electrode and the one or more of the brain tissue electrodes to clear the metal ions from the brain parenchyma into the CSF-filled space of the brain.

Inventive Concept 161. The apparatus according to Inventive Concept 137, wherein the substance includes tau protein, and wherein the control circuitry is configured to drive the CSF electrode and the one or more of the brain tissue electrodes to clear the tau protein from the brain parenchyma into the CSF-filled space of the brain.

Inventive Concept 162. The apparatus according to Inventive Concept 137, wherein the control circuitry is configured to drive the CSF electrode and the one or more of the brain tissue electrodes to clear the substance by applying non-excitatory current between the CSF electrode and the one or more of the brain tissue electrodes.

There is further provided, in accordance with an Inventive Concept 163 of the present invention, apparatus including an electrical brain treatment system, which includes:
- a parenchymal electrode, configured to be implanted in direct physical contact with brain tissue of a subject identified as at risk of or suffering from a disease, the brain tissue selected from the group consisting of: brain parenchyma and meninges of the brain;
- a cerebrospinal fluid (CSF) electrode, configured to be implanted in a CSF-filled space of the brain, the CSF-filled space selected from the group consisting of a ventricular system and a subarachnoid space; and
- control circuitry, which is electrically coupled to the parenchymal electrode and the CSF electrode, and which is configured to:
    - during amyloid-beta-clearance states, clear beta amyloid from the brain parenchyma into the CSF-filled space by applying direct current between the parenchymal electrode and the CSF electrode, with a negative charge at the parenchymal electrode and a positive charge at the CSF electrode, wherein the amyloid-beta-clearance states have an average duration of at least 5 minutes,
    - during metal-ion-clearance states, clear metal ions from the brain parenchyma into the CSF-filled space by applying direct current between the parenchymal electrode and the CSF electrode, with a positive charge at the parenchymal electrode and a negative charge at the CSF electrode, wherein the metal-ion-clearance states have an average duration of at least 1 minute, and
    - set an aggregate duration of the amyloid-beta-clearance states during a period to equal at least 4 times an aggregate duration of the metal-ion-clearance states during the period, the period having a duration of at least 30 days.

Inventive Concept 164. The apparatus according to Inventive Concept 163, wherein the control circuitry is configured to set the aggregate duration of the amyloid-beta-clearance states during the period to equal at least 9 times the aggregate duration of the metal-ion-clearance states during the period.

Inventive Concept 165. The apparatus according to Inventive Concept 163, wherein the control circuitry is configured to set the aggregate duration of the amyloid-beta-clearance states during the period to equal to no more than 100 times the aggregate duration of the metal-ion-clearance states during the period.

Inventive Concept 166. The apparatus according to Inventive Concept 163, wherein the control circuitry is configured to set the average duration of the amyloid-beta-clearance states to be at least one hour.

Inventive Concept 167. The apparatus according to Inventive Concept 163, wherein the control circuitry is configured to set the average duration of the metal-ion-clearance states to be at least 2 minutes.

Inventive Concept 168. The apparatus according to Inventive Concept 163, wherein the control circuitry is configured to assume the amyloid-beta-clearance states during nighttime, and the metal-ion-clearance states during daytime.

Inventive Concept 169. The apparatus according to Inventive Concept 163, wherein the control circuitry is configured to assume respective rest states after concluding the amyloid-beta-clearance states before beginning the respective subsequent metal-ion-clearance states.

Inventive Concept 170. The apparatus according to Inventive Concept 169, wherein an average duration of the rest states equals at least 5 minutes.

Inventive Concept 171. The apparatus according to Inventive Concept 163, wherein the average duration of the amyloid-beta-clearance states is less than 8 hours.

Inventive Concept 172. The apparatus according to Inventive Concept 163, wherein the average duration of the metal-ion-clearance states is less than one hour.

Inventive Concept 173. The apparatus according to Inventive Concept 163, wherein the control circuitry is configured to apply the direct current with a first average strength during the amyloid-beta-clearance states and a second average strength during the metal-ion-clearance states, the first average strength equal to at least 150% of the second average strength.

Inventive Concept 174. The apparatus according to Inventive Concept 163, wherein the electrical brain treatment system further includes a midplane treatment electrode, adapted to be disposed in or over a superior sagittal sinus, wherein the control circuitry is configured to clear the beta amyloid from the CSF-filled space of the brain to the superior sagittal sinus, by applying a treatment current between the midplane treatment electrode and the CSF electrode.

Inventive Concept 175. The apparatus according to Inventive Concept 163, wherein the control circuitry is configured to apply the direct current using an average voltage of less than 1.2 V during the amyloid-beta-clearance states and during the metal-ion-clearance states.

Inventive Concept 176. The apparatus according to Inventive Concept 163, wherein the disease is Alzheimer's disease, and wherein the parenchymal electrode is configured to be implanted in the subject identified as at risk of or suffering from Alzheimer's disease.

Inventive Concept 177. The apparatus according to Inventive Concept 163, wherein the disease is cerebral amyloid angiopathy (CAA), and wherein the parenchymal electrode is configured to be implanted in the subject identified as at risk of or suffering from CAA.

Inventive Concept 178. The apparatus according to Inventive Concept 163, wherein the CSF-filled space of the brain is the ventricular system, and wherein the CSF electrode is a ventricular electrode, configured to be implanted in the ventricular system.

Inventive Concept 179. The apparatus according to Inventive Concept 163, wherein the CSF-filled space of the brain is the subarachnoid space, and wherein the CSF electrode is a subarachnoid electrode, configured to be implanted in the subarachnoid space.

Inventive Concept 180. The apparatus according to Inventive Concept 163, wherein the parenchymal electrode is configured to be implanted within the brain parenchyma.

Inventive Concept 181. The apparatus according to Inventive Concept 180, wherein the parenchymal electrode is configured to be implanted in white matter of the brain.

Inventive Concept 182. The apparatus according to Inventive Concept 163, wherein the parenchymal electrode is configured to be implanted in direct physical contact with the meninges of the brain.

Inventive Concept 183. The apparatus according to Inventive Concept 163, wherein the control circuitry is configured to drive the parenchymal electrode and the CSF electrode to clear the beta amyloid during the amyloid-beta-clearance states by applying non-excitatory current between the parenchymal electrode and the CSF electrode.

Inventive Concept 184. The apparatus according to Inventive Concept 163, wherein the control circuitry is configured to drive the parenchymal electrode and the CSF electrode to apply the direct current as a series of pulses during the amyloid-beta-clearance states.

Inventive Concept 185. The apparatus according to Inventive Concept 184, wherein the control circuitry is configured to apply the direct pulses with an average amplitude of between 0.25 and 0.5 mA, an average pulse width of between 0.5 and 2 ins, and an average frequency of between 1 and 5 Hz.

There is still further provided, in accordance with an Inventive Concept 186 of the present invention, a method including:
  implanting an electrical lead of an electrical brain treatment system in a brain of a subject identified as at risk of or suffering from at least one disease, the electrical lead including an elongate support structure; deep brain stimulation (DBS) electrodes, fixed to the elongate support structure; and a parenchymal electrode, fixed to the elongate support structure at least 3 cm from a closest one of the DBS electrodes, wherein implanting the electrical lead includes implanting the DBS electrodes in a deep brain structure and implanting the parenchymal electrode in direct physical contact with brain tissue selected from the group consisting of: brain parenchyma and meninges of the brain;
  implanting a cerebrospinal fluid (CSF) electrode of the electrical brain treatment system in a CSF-filled space of the brain, the CSF-filled space selected. from the group consisting of: a ventricular system and a subarachnoid space; and
  activating control circuitry, which is electrically coupled to the electrical lead, to (i) drive the DBS electrodes to apply DBS to the deep brain structure, and (ii) drive the parenchymal electrode and the CSF electrode to clear a substance from the brain parenchyma into the CSF-filled space.

There is additionally provided, in accordance with an Inventive Concept 187 of the present invention, a method including:
  implanting a first electrical lead of an electrical brain treatment system in a brain of a subject identified as at risk of or suffering from at least one disease, the first electrical lead including a first elongate support structure; deep brain stimulation (DBS) electrodes, fixed to the first elongate support structure; and a cerebrospinal fluid (CSF) electrode, fixed to the first elongate support structure, wherein implanting the first electrical lead includes implanting the DBS electrodes in a deep brain structure and implanting the CSF electrode in a CSF-filled space of the brain, the CSF-filled space selected from the group consisting of: a ventricular system and a subarachnoid space;
  implanting a second electrical lead of the electrical brain treatment system in the brain, the second electrical lead including a second elongate support structure; and a parenchymal electrode, fixed to the second elongate support structure, wherein implanting the second electrical lead includes implanting the parenchymal electrode in direct physical contact with brain tissue selected from the group consisting of: brain parenchyma and meninges of the brain; and
  activating control circuitry, which is electrically coupled to the first and the second electrical leads, and to (i) drive the DBS electrodes to apply deep brain stimulation (DBS) to the deep brain structure, and (ii) drive the parenchymal electrode and the CSF electrode to clear a substance from the brain parenchyma. into the CSF-filled space.

There is yet additionally provided, in accordance with an Inventive Concept 188 of the present invention, a method including:

implanting an electrical lead of an electrical brain treatment system in a brain of a subject identified as at risk of or suffering from at least one disease, the electrical lead including an elongate support structure; and brain tissue electrodes, fixed to the elongate support structure, wherein implanting the electrical lead includes implanting the brain tissue electrodes in a deep brain structure;

implanting a cerebrospinal fluid (CSF) electrode of the electrical brain treatment system in a CSF-filled space of the brain, the CSF-filled space selected from the group consisting of: a ventricular system and a subarachnoid space; and activating control circuitry, which is electrically coupled to the electrical lead, to (i) drive one or more of the brain tissue electrodes to apply deep brain stimulation (DBS) to the deep brain structure, and (ii) drive the CSF electrode and one or more of the brain tissue electrodes to clear a substance from brain parenchyma into the CSF-filled space.

There is also provided, in accordance with an Inventive Concept 189 of the present invention, a method including:

implanting a parenchymal electrode of an electrical brain treatment system in direct physical contact with brain tissue of a subject identified as at risk of or suffering from a disease, the brain tissue selected from the group consisting of: brain parenchyma and meninges of the brain;

implanting a cerebrospinal fluid (CSF) electrode of the electrical brain treatment system in a CSF-tilled space of the brain, the CSF-filled space selected from the group consisting of a ventricular system and a subarachnoid space; and activating control circuitry, which is electrically coupled to the parenchymal electrode and the CSF electrode, to:

during amyloid-beta-clearance states, clear beta amyloid from the brain parenchyma into the CSF-filled space by applying direct current between the parenchymal electrode and the CSF electrode, with a negative charge at the parenchymal electrode and a positive charge at the CSF electrode, wherein the amyloid-beta-clearance states have an average duration of at least 5 minutes, during metal-ion-clearance states, clear metal ions from the brain parenchyma into the CSF-filled space by applying direct current between the parenchymal electrode and the CSF electrode, with a positive charge at the parenchymal electrode and a negative charge at the CSF electrode, wherein the metal-ion-clearance states have an average duration of at least 1 minute, and set an aggregate duration of the amyloid-beta-clearance states during a period to equal at least 4 times an aggregate duration of the metal-ion-clearance states during the period, the period having a duration of at least 30 days.

The present invention will be more fully understood from the following detailed description of embodiments thereof taken together with the drawings, in which:

DETAILED DESCRIPTION OF APPLICATIONS

Figure 1A:
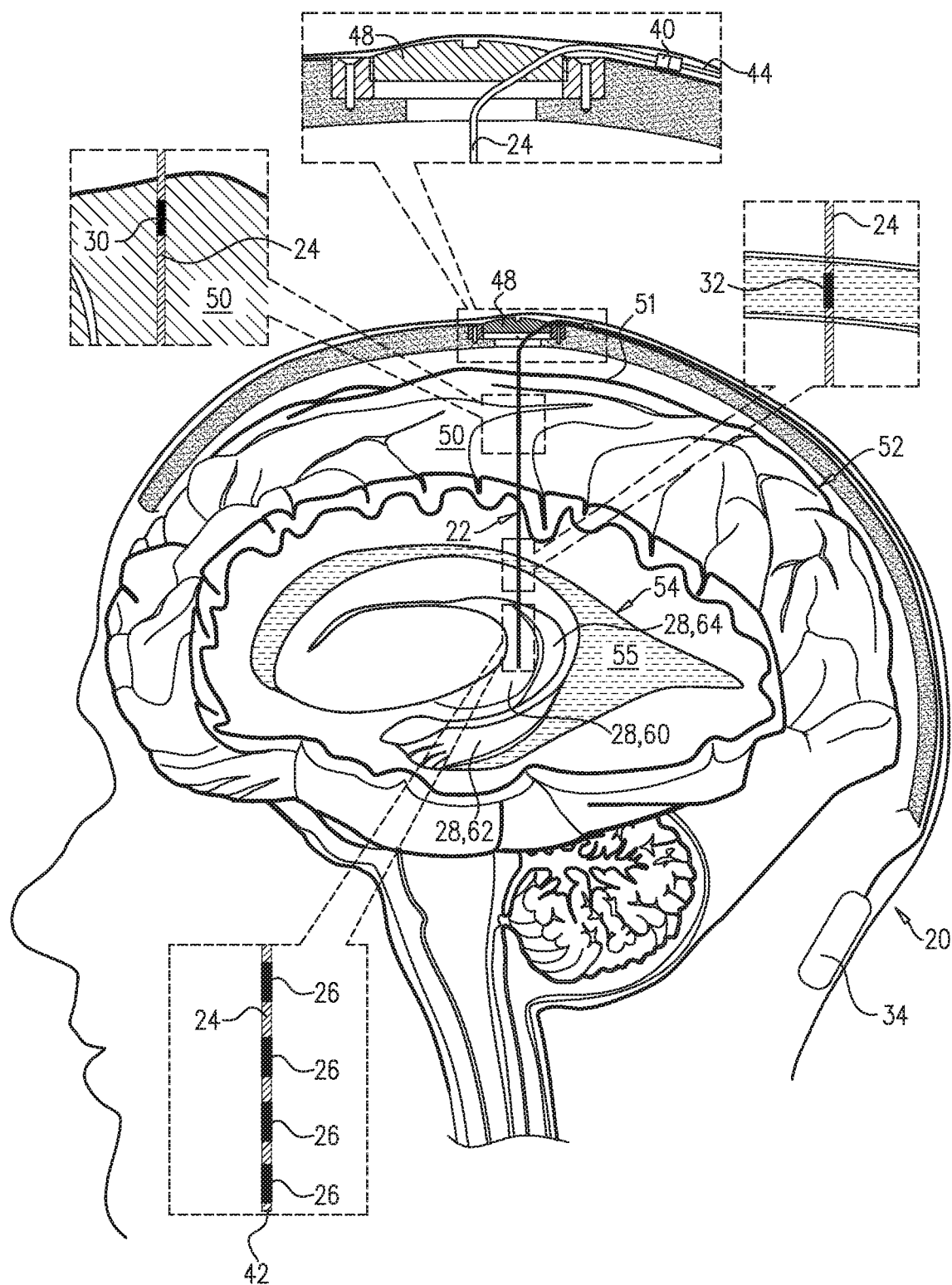
FIGS. 1A-D are schematic illustrations of an electrical brain treatment system, in accordance with respective applications of the present invention.

FIGS. 1A-D are schematic illustrations of an electrical brain treatment system 20, in accordance with respective applications of the present invention. Electrical brain treatment system 20 typically comprises an electrical lead 22, which is configured to be implanted in a brain 52 of a subject identified as at risk of or suffering from at least one disease. For some applications, the at least one disease includes Alzheimer's disease, Alzheimer's disease and Parkinson's disease, and cerebral amyloid angiopathy (CAA).

Electrical lead 22 typically comprises:

an elongate support structure 24 (which may be considered a lead body), which typically has a length of at least 3 cm, no more than 25 cm (e.g., no more than 15 cm), and/or between 3 and 25 cm, such as between 3 and 15 cm; elongate support structure 24 comprises a biocompatible, non-conducting material such as, for example, a polymeric material, e.g., silicone, polyurethane, polyethylene, polyurea, or polyurethane-urea;

deep brain stimulation (DBS) electrodes 26, fixed to elongate support structure 24, and configured to be implanted in a deep brain structure 28; and a parenchymal electrode 30, fixed to elongate support structure 24 at least 0.5 cm, e.g., at least 1 cm, such as at least 3 cm from a closest one of DBS electrodes 26, and configured to be implanted in direct physical contact with (e.g., within) brain tissue selected from the group consisting of: brain parenchyma 50 (as shown) and meninges 51 of brain 52 (configuration not shown).

Optionally, elongate support structure 24 is shaped so as to define a lumen, into which a stylet (e.g., a rigid stylet) may be temporarily disposed during insertion and positioning of the elongate support structure in brain 52, as is known in the DBS lead art.

Optionally, any of the electrodes described herein may comprise ring electrodes, as is known in the DBS lead art. Typically, the electrodes described herein comprise a metal, an alloy, a conductive oxide, or any other suitable conductive biocompatible material. Examples of suitable materials include, but are not limited to, platinum, platinum iridium alloy, iridium, titanium, or tungsten.

For some applications in which parenchymal electrode 30 is configured to be implanted within brain parenchyma 50, parenchymal electrode 30 is configured to be implanted in white matter of brain 52. Alternatively, for some applications in which parenchymal electrode 30 is configured to be implanted within brain parenchyma 50, parenchymal electrode 30 is configured to be implanted a cerebral cortex of brain 52 (i.e., in gray matter).

Electrical brain treatment system 20 further comprises a cerebrospinal fluid (CSF) electrode 32, configured to be implanted in a CSF-filled space of brain 52, the TO CSF-filled space selected from the group consisting of: a ventricular system 54 of brain 52 or a subarachnoid space 144 (labeled in FIG. 4) (e.g., cisterns of subarachnoid space 144). For example, CSF electrode 32 may be implanted using techniques known for implanting hydrocephalus shunts, mutatis mutandis. As used in the present application, including in the claims, ventricular system 54 includes and is limited to lateral ventricles 55, a third ventricle, a fourth ventricle, a cerebral aqueduct, interventricular foramina, a median aperture, and left and right lateral apertures.

Typically, electrical brain treatment system 20 further comprises a cap 48, which is configured to be attached to the skull at a burr hole site through which electrical lead 22 is introduced through the skull. Cap 48 is configured to secure electrical lead 22 to the skull at the entry site to ensure that the electrical lead does not migrate and the positions of the therapeutic contacts remain constant in brain 52. Optionally, cap 48 comprises locking elements for preventing movement of electrical lead 22. Cap 48 may implement techniques known in the DBS cap art, such as described for example in U.S. Pat. No. 6,044,304 to Baudino, U.S. Pat. No. 7,949,410 to Rodriguez, U.S. 2015/0039063 to Okun et al., all of which are incorporated herein by reference.

Optionally, electrical brain treatment system 20 comprises a plurality of electrical leads 22, such as two electrical leads 22, which are implanted, for example, in respective hemispheres of brain 52. Alternatively or additionally, electrical brain treatment system 20 optionally comprises a plurality of CSF electrodes 32, such as two CSF electrodes 32, which are implanted, for example, in respective hemispheres of brain 52.

Electrical brain treatment system 20 still further comprises control circuitry 34, which is electrically coupled to electrical lead 22, and which is typically configured to (a) drive DBS electrodes 26 to apply DBS to deep brain structure 28, and (b) drive parenchymal electrode 30 and CSF electrode 32 to clear a substance from brain parenchyma 50 into the CSF-filled space. For some applications, the substance comprises amyloid beta, metal ions, a tau protein, and/or a waste substance. As used in the present application, including in the claims, clearing a substance from brain parenchyma 50 is to be understood as including clearing a portion of the substance, without clearing all of the substance. Typically, in order to clear the substance, control circuitry 34 applies a voltage or a current between parenchymal and CSF electrodes 30 and 32 (i.e., control circuitry 34 regulates the voltage or the current).

Typically, a healthcare worker, such as a physician, activates control circuitry 34 to provide the functions described herein. Activating the control unit may include configuring parameters and/or functions of the control circuitry (such as using a separate programmer or external controller), or activating the control unit to perform functions pre-programmed in the control circuitry. Control circuitry 34 typically comprises appropriate memory, processor(s), and hardware running software that is configured to provide the functionality of control circuitry described herein.

Current may flow generally through tissue that is located between parenchymal electrode 30 and CSF electrode 32. Alternatively or additionally, at least a portion of the current may flow between (a) parenchymal electrode 30 and (b) an area of the CSF-filled space (e.g., ventricular system 54) nearest parenchymal electrode 30. The inventors have appreciated that because of the low electrical resistance of cerebrospinal fluid (CSF) in the CSF-filled space, such as ventricular system 54, the ventricles are to some extent a single entity electrically. Therefore, a large portion of the current flows to the nearest portion of ventricular system 54, even if CSF electrode 32 is implanted in a ventricle remote from parenchymal electrode 30.

For some applications, the voltage applied between the electrodes may clear the substance electrophoretically, because of a positive or negative charged interface between the surface of the particles of the substance and the surrounding brain tissue fluids. For these applications, the voltage applied between the electrodes causes a potential difference between brain parenchyma 50 and the CSF-filled space, such as ventricular system 54, which causes movement of the substance from brain parenchyma 50 to the CSF-filled space, such as ventricular system 54. Alternatively or additionally, for some applications, the voltage applied between the electrodes may clear the substance electroosmotically, because of a positive or negative charge of fluid in the parenchyma. For these applications, the voltage applied between the electrodes causes a potential difference between brain parenchyma 50 and the CSF-filled space, such as ventricular system 54, which causes increased flow from brain parenchyma 50 to the CSF-filled space, such as ventricular system 54, and thus increased transport of the substance from parenchyma 50 to the CSF-filled space, such as ventricular system 54.

For sonic applications, control circuitry 34 is configured to be implanted subcutaneously, such under skin of the skull of the subject if the housing containing the control circuitry is small (such as shown), or elsewhere in the subject's body (not shown), such as in the upper chest, if the housing of the control circuitry is larger (e.g., includes batteries), with leads through the neck, or optionally in the head. For other applications, control circuitry 34 is incorporated into cap 48.

For any of these applications, control circuitry 34 may be driven by an external controller that is in wireless or wired communication with control circuitry 34. For sonic applications, the external controller is mounted on a bed of the subject (e.g., disposed within a mattress), and is configured to activate control circuitry 34 only at night, and/or only when the subject is sleeping. Such nighttime activation may to some degree mimic the natural timing of clearance of the substance (e.g., amyloid beta or tau protein) during sleep, during which the extracellular spaces are wider than during wakefulness, which allows more interstitial fluid (ISF) flow within brain 52.

For other applications, control circuitry 34 is configured to be disposed externally to the subject.

Figure 1B:
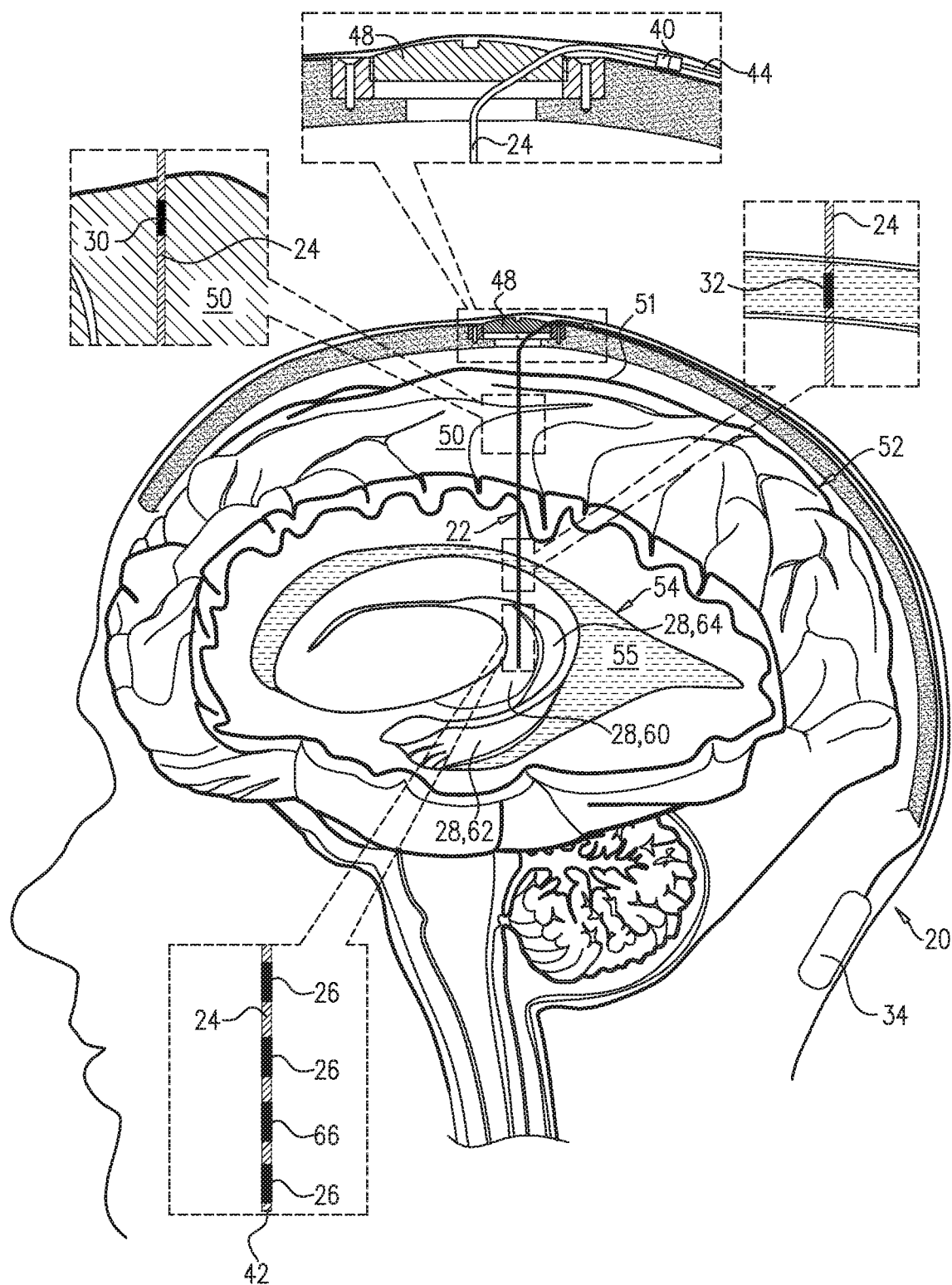
Figure 1C:
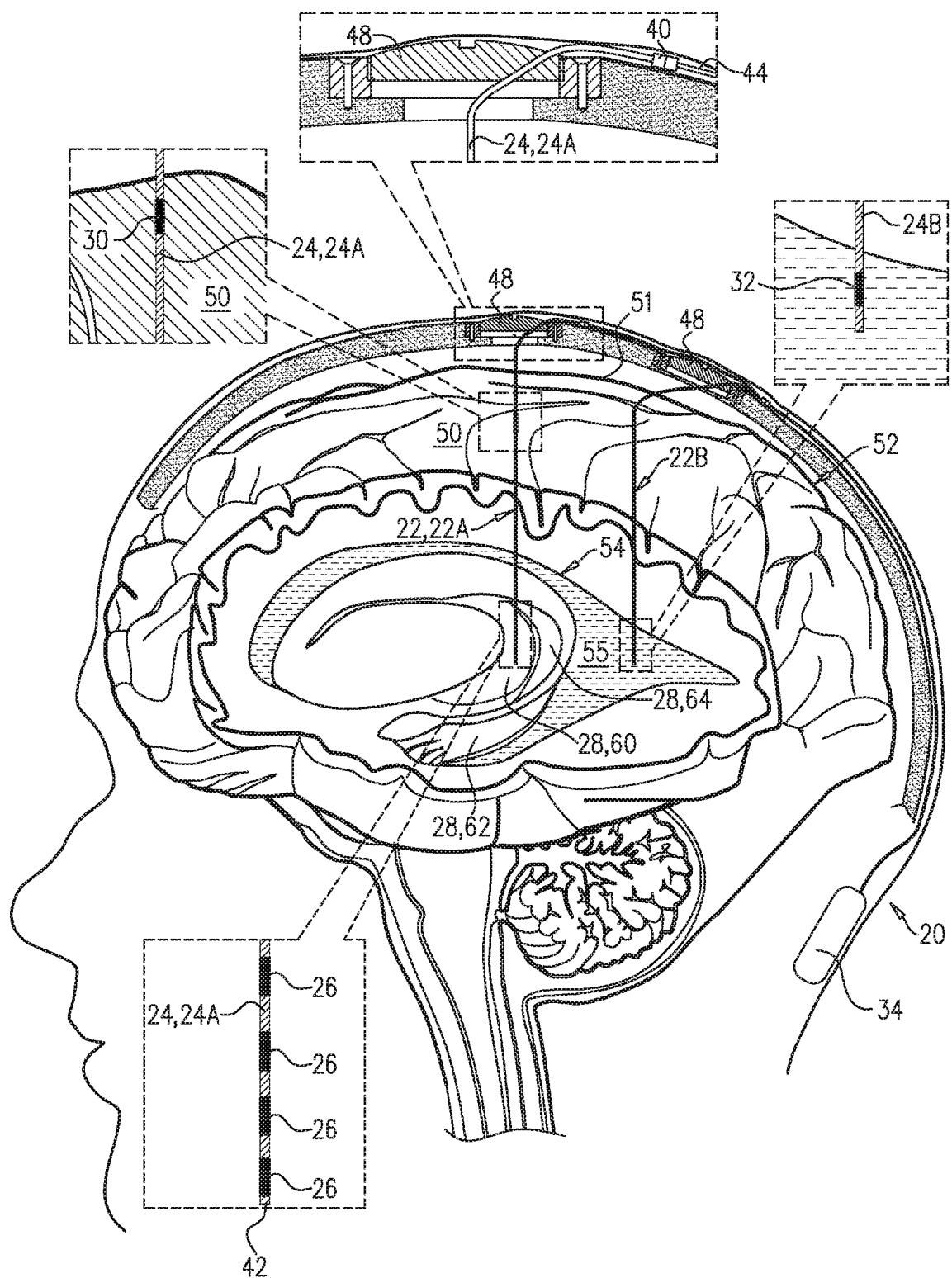

Reference is made to FIGS. 1A-C. For some applications, such as for treating Parkinson's disease by the DBS, deep brain structure 28 is selected from the group consisting of: a thalamus 60, a subthalamic nucleus (STN), a globus pallidus (GPi) (e.g., a pars interna of the GPi), an intermediate thalamus (VIM) in thalamus 60, caudal zona incerta, and pallidofugal fibers medial to the STN.

Figure 1D:
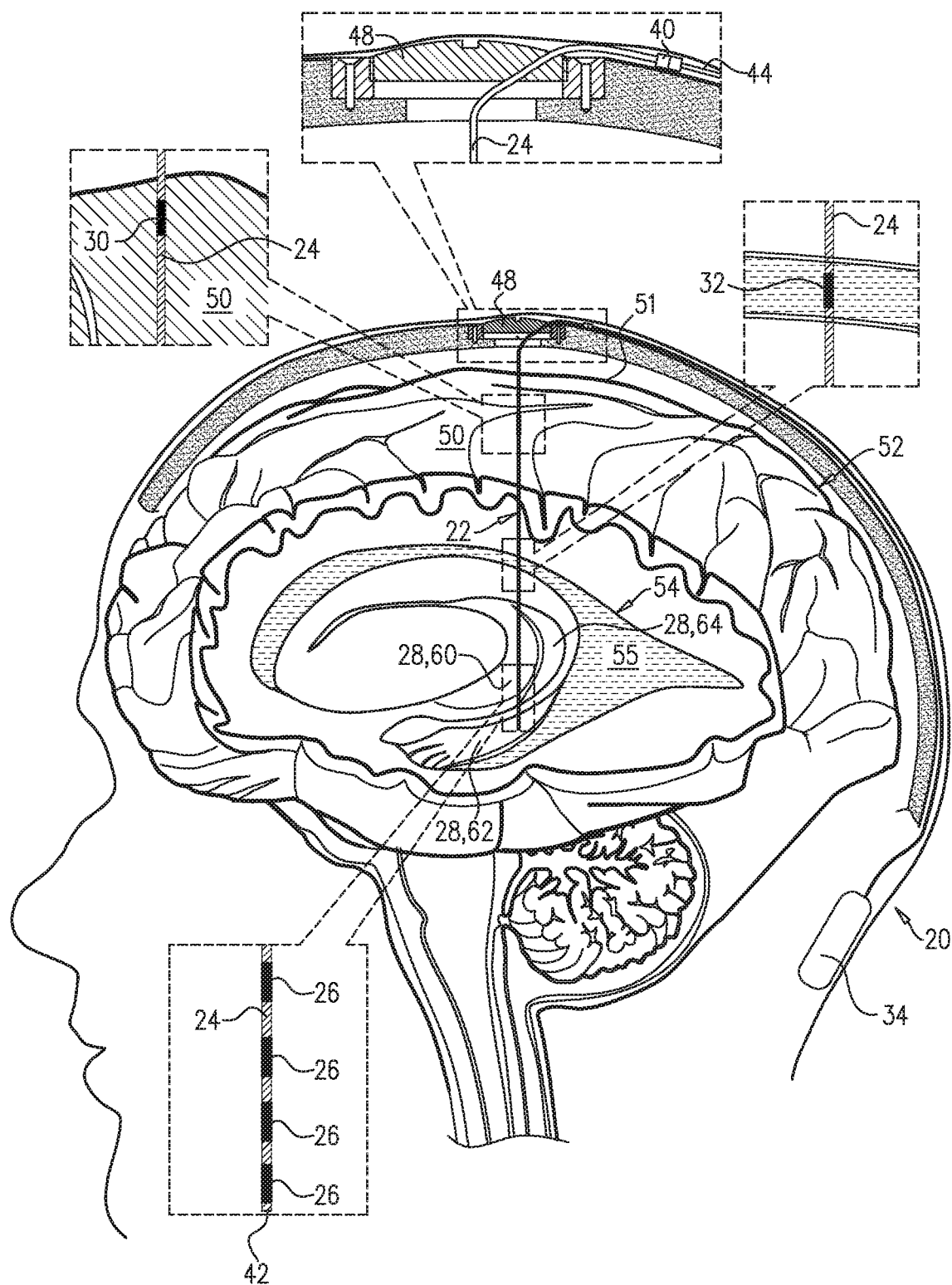

Reference is made to FIG. 1D. For some applications, such as for treating Alzheimer's disease by the DBS, deep brain structure 28 is selected from the group consisting of: a hippocampus 62 (as shown) and a fornix 64 (configuration not shown). The configurations of electrical brain treatment system 20 shown in FIGS. 1B-C may be implemented in combination with the configuration shown in FIG. 1D.

For some applications, the substance includes amyloid beta, and control circuitry 34 is configured to drive parenchymal electrode 30 and CSF electrode 32 to clear the amyloid beta from brain parenchyma 50 into the CSF-filled space of brain 52. For some applications, the substance includes metal ions, and wherein control circuitry 34 is configured to drive parenchymal electrode 30 and CSF electrode 32 to clear the metal ions from brain parenchyma 50 into the CSF-filled space of brain 52. For some applications, the substance includes tau protein, and wherein control circuitry 34 is configured to drive parenchymal electrode 30 and CSF electrode 32 to clear the tau protein from brain parenchyma 50 into the CSF-filled space of brain 52.

For some applications, control circuitry 34 is configured to drive parenchymal electrode 30 and CSF electrode 32 to clear the substance by applying direct current (DC) between parenchymal electrode 30 and CSF electrode 32. As used in the present application, including in the claims, direct current means a current having a constant polarity; the amplitude of the direct current may or may not vary over time, and may sometimes be zero. Typically, electrical charge does not build up at either electrode because of discharge between the pulses.

Alternatively, for other applications, control circuitry 34 is configured to drive parenchymal electrode 30 and CSF electrode 32 to clear the substance by applying, between parenchymal electrode 30 and CSF electrode 32, current predominantly with a first polarity, but also partially with a second polarity opposite the first polarity. The relatively small portion of current applied with the second polarity may help release at least a portion of material that may build up on the electrodes, such as at least a portion of amyloid beta that may build up on CSF electrode 32, or another substance (e.g., metal ions or tau protein) that may build up on the CSF electrode after the substance has been cleared from the brain parenchyma 50 by application of the current with the first polarity. The current applied with the second polarity thus may release any amyloid beta built up on CSF electrode 32 from CSF electrode 32 into the CSF of the CSF-filled space of brain 52. The CSF-filled space then typically naturally clears the amyloid beta. In addition, the current applied with the second polarity is typically not applied with sufficient charge (e.g., not long enough) to return to the brain parenchyma 50 a meaningful amount of the amyloid beta released from CSF electrode 32; for example, the current applied with the second polarity may be configured to return to the brain parenchyma 50 no more than 10% by weight, such as no more than 1% by weight (e.g., substantially none), of the amyloid beta released from CSF electrode 32.

Typically, control circuitry 34 is configured to apply at least 80% (e.g., at least 90%, such as at least 95%, e.g., at least 99%) but less than 100% of the charge (e.g., measured in coulombs) of the current with the first polarity (e.g., less than 99.99%, such as less than 99.9%, and the remainder of the charge with the second polarity. The difference in charges may be achieved, for example, by:
  applying the current with the first polarity for a longer aggregate amount of time than with the second polarity, such as at least 5 times longer, e.g., at least 10 times longer, such as at least 20 times longer, e.g., at least 100 times longer,
  applying the current with the first polarity with a greater amperage than with the second polarity, such as at least 5 times greater, e.g., at least 10 times greater, such as at least 20 times greater, e.g., at least 100 times greater, and/or
  any combination of the above two parameters.

It is noted that applying direct current is equivalent to applying 100% of the charge of the current with the first polarity. Likewise, applying less than 100% of the charge of the current with the first polarity is different from applying direct current.

For some of the applications in which control circuitry 34 applies a voltage between parenchymal and CSF electrodes 30 and 32 in a series of DC pulses, the resulting current decays, e.g., because of the effects of tissue electrolytes. The current may decay by about two-thirds of its initial magnitude within tens of milliseconds after commencement of application of each pulse. In order to overcome this capacitance effect, control circuitry 34 is activated to apply the voltage intermittently, in order to provide time periods between pulses during which the capacitance discharges.

For some applications in which control circuitry 34 is configured to apply direct current, control circuitry 34 is configured to apply the direct current with a negative charge at parenchymal electrode 30 and a positive charge at CSF electrode 32 for clearing amyloid beta. For some applications, control circuitry 34 is configured to apply the direct current with a positive charge at parenchymal electrode 30 and a negative charge at CSF electrode 32 for clearing metal ions.

For some applications in which control circuitry 34 is configured to apply current predominantly with a first polarity, control circuitry 34 is configured to apply the current with the first polarity with a negative charge at parenchymal electrode 30 and a positive charge at CSF electrode 32 for clearing amyloid beta. For some applications, control circuitry 34 is configured to apply the current with the first polarity with a positive charge at parenchymal electrode 30 and a negative charge at CSF electrode 32 for clearing metal ions.

For some applications in which control circuitry 34 is configured to apply direct current, control circuitry 34 is configured to drive parenchymal electrode 30 and CSF electrode 32 to apply the direct current as a series of pulses. For example, control circuitry 34 may be configured to apply the direct pulses with an average amplitude of at least 0.25 mA, no more than 0.5 mA, and/or between 0.25 and 0.5 mA, an average pulse width of at least 0.5 ms, no more than 2 ms, and/or between 0.5 and 2 ms, and an average frequency of at least 1 Hz, no more than 5 Hz, and/or between 1 and 5 Hz (e.g., between 1.5 and 3 Hz, such as between 1.5 and 2.5 Hz), or with the parameters described hereinbelow. Typically, control circuitry 34 is configured to apply the direct current using an average voltage of less than 1.2 V (such an amplitude may avoid electrolysis in the vicinity of one or more of the electrodes).

For some applications in which control circuitry 34 is configured to apply current predominantly with a first polarity, control circuitry 34 is configured to drive parenchymal electrode 30 and CSF electrode 32 to apply the current as a series of pulses. For example, control circuitry 34 may be configured to:
  apply the pulses with the first polarity with an average amplitude of at least 0.25 mA, no more than 0.5 mA, and/or between 0.25 and 0.5 mA, an average pulse width of at least 0.5 ms, no more than 2 ms, and/or between 0.5 and 2 ins, and an average frequency of at least 1 Hz, no more than 5 Hz, and/or between 1 and 5 Hz, or with the parameters described hereinbelow, and/or
  apply the pulses with the second polarity with an average amplitude of at least 0.01 mA (e.g., at least 0.025 mA), no more than 0.1 mA (e.g., no more than 0.05 mA), and/or between 0.01 mA (e.g., 0.025 mA) and 0.1 mA (e.g., 0.05 mA), an average pulse width of at least 0.025 ms (e.g., at least 0.05 ms), no more than 0.4 ms (e.g., no more than 0.2 ms), and/or between 0.025 ms 0.05 ins and 0.4 ins (e.g., 0,2 ins), and an average frequency of at least 0.01 Hz (e.g., at least 0.1 Hz, such as at least 1 Hz), no more than 5 Hz (e.g., no more than 1 Hz), and/or between 0.01 Hz (e.g., at least 0.1 Hz, such as at least 1 Hz) and 5 Hz (e.g., no more than 1 Hz), or with the parameters described hereinbelow.

For example, control circuitry 34 may be configured to alternatingly apply one or more pulses with the first polarity and one or more pulses with the second polarity. For example, control circuitry 34 may be configured to alternatingly apply a single pulse with the first polarity and a single pulse with the second polarity, or to alternatingly apply a plurality of pulses with the first polarity and a single pulse with the second polarity. In any case, control circuitry 34 is typically configured to apply the one or more pulses with the first polarity for a substantially longer time than it applies the one or more pulses with the second polarity. For example, 1-10, 10-100, or more pulses with the first polarity may be applied, without any intervening pulses of the second polarity being applied. That is, for some applications, each pulse with the first polarity is followed by a far shorter pulse or pulse train of the second polarity, a plurality of pulses of the first polarity are followed by one or more pulses of the second polarity that have a shorter total duration, and/or a frequency of the pulses of the second polarity is less than a frequency of the pulses of the first polarity, such as no more than 20%, e.g., no more than 15%, such as no more than 10%, of the frequency of the pulses of the first polarity (by way of example and not limitation, if the frequency of the pulses of the first polarity is 2 Hz, the frequency of the pulses of the second polarity may be 0.2 Hz).

Typically, control circuitry 34 is configured to apply the current using an average voltage of less than 1.2 V (such an amplitude may avoid electrolysis in the vicinity of one or more of the electrodes).

Typically, control circuitry 34 is configured to drive parenchymal electrode 30 and CSF electrode 32 to clear the substance by applying a non-excitatory current between parenchymal electrode 30 and CSF electrode 32, i.e., the current does not cause propagation of action potentials. Thus, in these applications, control circuitry 34 is activated to set parameters of the current such that the current does not affect, or only minimally affects, neuronal activity. Alternatively, the applied current does excite brain tissue, such as to a small extent.

Typically, control circuitry 34 is configured to drive DBS electrodes 26 to apply the DBS as a train of pulses. For example, the DBS may be applied with a frequency of between 5 and 200 Hz, such as between 100 and 200 Hz, e.g., between 100 and 150 Hz, such as between 120 and 140 Hz; an amplitude of between 10 microamps and 1 mA; a mean voltage of between 1 and 2.5 V, such as between 1.2 and 2.3 V; and/or a pulse duration of between 10 and 250 microseconds, such as between 50 and 200 microseconds. For some applications, the DBS is applied as a train of direct current (DC) pulses, as is conventional in DBS, while for other applications, the DBS is applied as a train of biphasic pulses, as is known in recent DBS research. If applied as the train of biphasic pulses, the phases may have the same or different amplitudes.

For some applications, control circuitry 34 is configured to drive CSF electrode 32 and one or more of DBS electrodes 26 to clear the substance from brain parenchyma 50 into the CSF-filled space, typically during at least some time periods in which control circuitry 34 is not driving DBS electrodes 26 to apply the DBS to deep brain structure 28. In other words, one or more of the DBS electrodes are used at different times for applying DBS and for substance clearance.

Figure 2A:
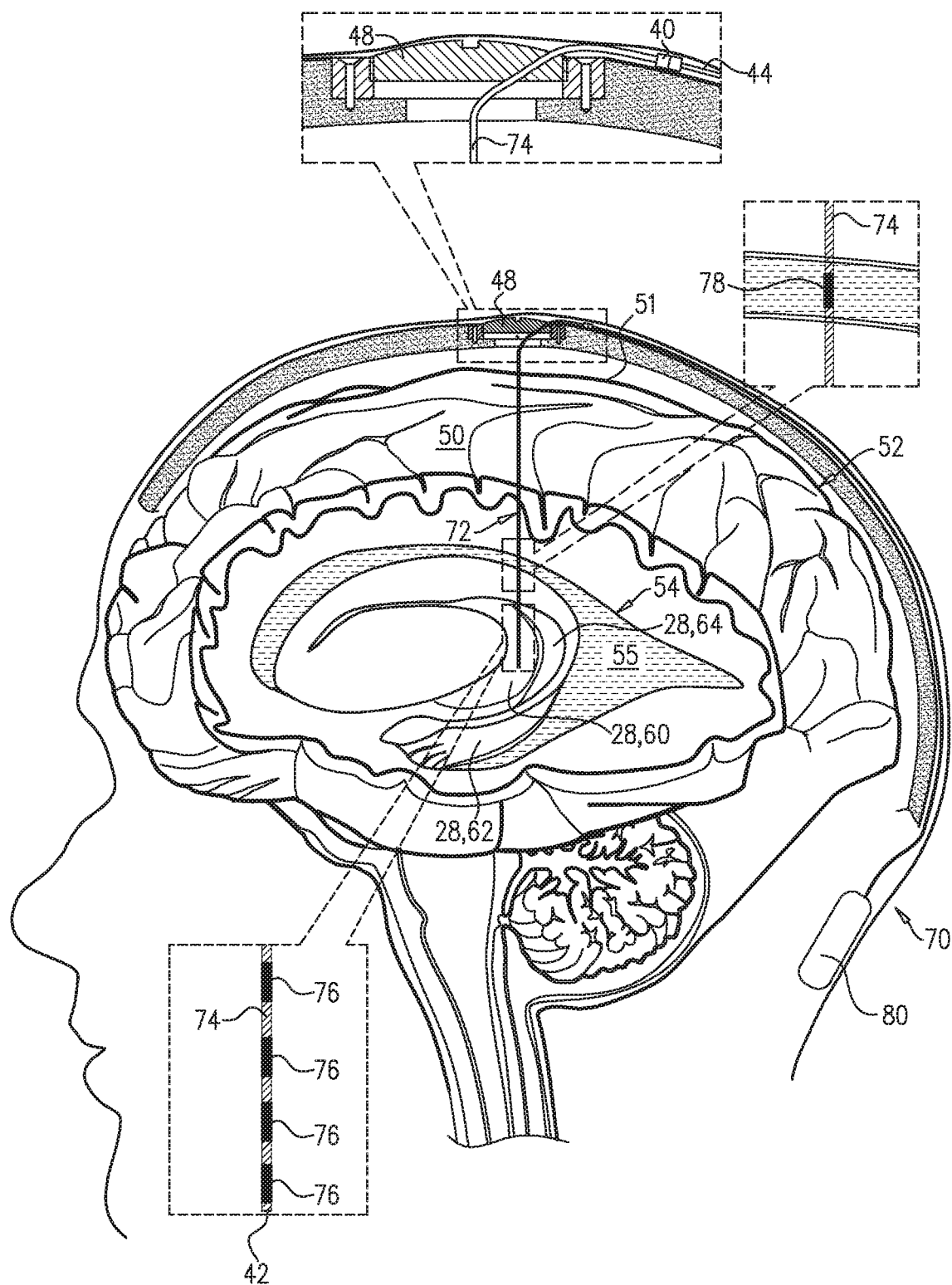
FIGS. 2A-B are schematic illustrations of another electrical brain treatment system, in accordance with respective applications of the present invention.
Figure 2B:
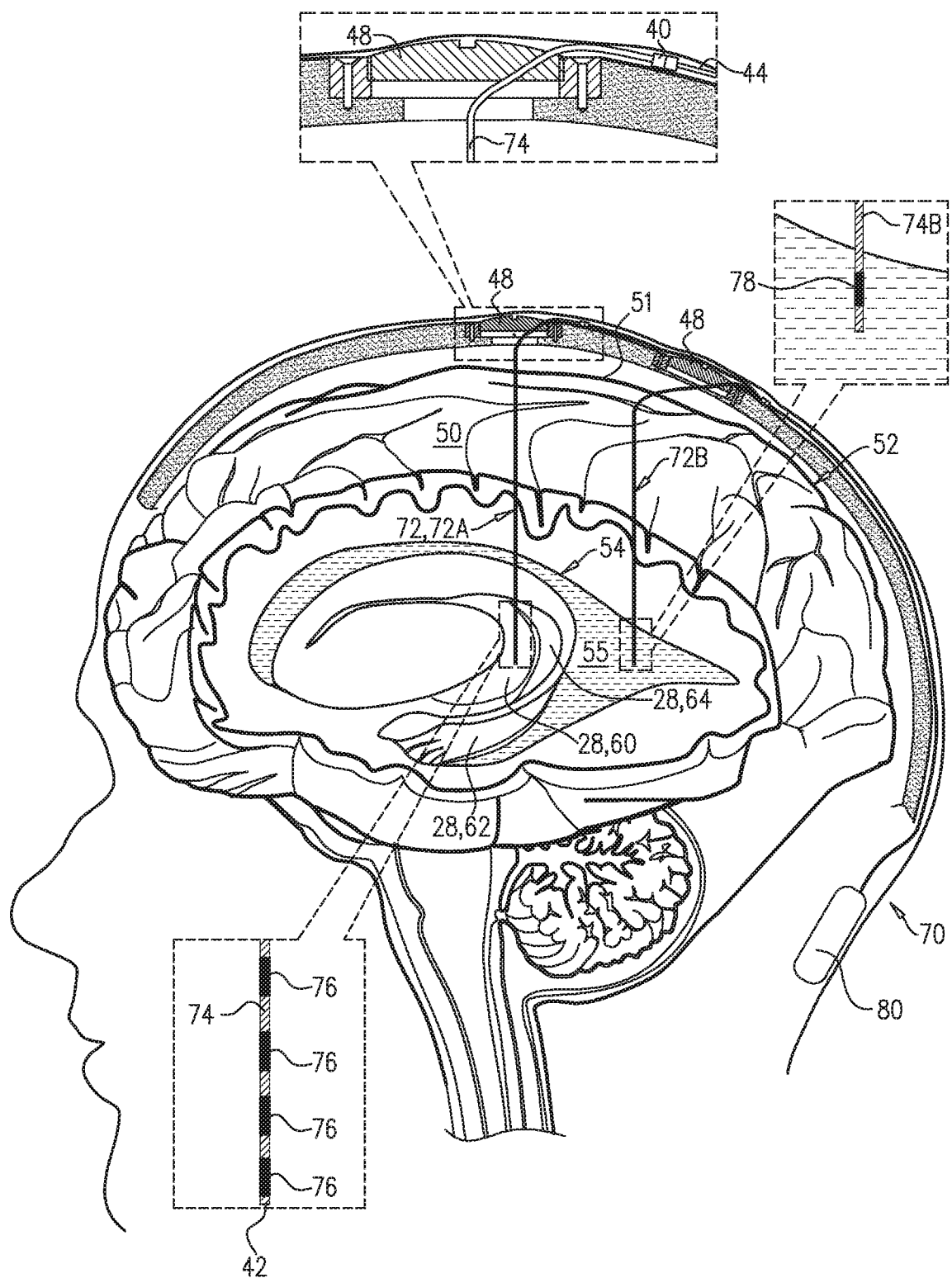

Reference is made to FIGS. 1A, 2B, and 2D. For some applications, such as shown in these figures, CSF electrode 32 is fixed to elongate support structure 24, typically longitudinally between parenchymal electrode 30 and DBS electrodes 26.

Reference is made to FIG. 1B. For some applications, electrical lead 22 further comprises a supplemental clearance electrode 66, which is fixed to elongate support structure 24 no more proximally than a proximal-most one of DBS electrodes 26. Control circuitry 34 is configured to drive supplemental clearance electrode 66 and CSF electrode 32 to clear the substance from brain parenchyma 50 into the CSF-filled space, either in alternation with or simultaneously with driving parenchymal electrode 30 and CSF electrode 32 to clear the substance from brain parenchyma 50 into the CSF-filled space.

Reference is made to FIG. 1C. For some applications, such as shown in FIG. 1C, electrical lead 22 is a first electrical lead 22A, and elongate support structure 24 is a first elongate support structure 24A. Electrical brain treatment system 20 further comprises a second electrical lead 22B, which comprises a second elongate support structure 24B (e.g., having a length of at least 3 cm, no more than 25 cm, and/or between 3 and 25 cm), CSF electrode 32 is fixed to second elongate support structure 24B. Control circuitry 34 is electrically coupled to first and second electrical leads 22A and 22B. For example, second electrical lead 22B may be implanted using techniques known for implanting hydrocephalus shunts, mutatis mutandis.

Reference is again made to FIGS. 1A-D, Elongate support structure 24 has a proximal end 40 and a distal end 42. DBS electrodes 26 and parenchymal electrode 30 (and CSF electrode 32 in the configuration of FIGS. 1A, 1B, and 1D) are electrically coupled to control circuitry 34 via proximal end of elongate support structure 24. Typically, DBS electrodes 26 are fixed to elongate support structure 24 near (e.g., within 3 cm, such as within 2 cm of) distal end 42. For some applications, electrical brain treatment system 20 further comprises a connection cable 44 (sometimes called an "extension" in the art) that is coupled to control circuitry 34 and to proximal end 40 of electrical lead 22.

Reference is now made to FIGS. 2A-B, which are schematic illustrations of an electrical brain treatment system 70, in accordance with respective applications of the present invention. Except as described below, electrical brain treatment system 70 may implement any of the features of electrical brain treatment system 20, described hereinabove with reference to FIGS. 1A-D.

Electrical brain treatment system 70 typically comprises an electrical lead 72, which is configured to be implanted in brain 52 of a subject identified as at risk of or suffering from at least one disease, such as the diseases described above with reference to FIGS. 1A-D, Electrical lead 72 comprises an elongate support structure 74, and brain tissue electrodes 76, fixed to elongate support structure 74, and configured to be implanted in deep brain structure 28, which typically includes parenchyma.

Electrical brain treatment system. 70 further comprises a cerebrospinal fluid (CSF) electrode 78, configured to be implanted in a CSF-filled space of brain 52, the CSF-filled space selected from the group consisting of ventricular system 54 and subarachnoid space 144.

Electrical brain treatment system 70 still further comprises control circuitry 80, which is electrically coupled to electrical lead 72, and which is typically configured to (a) drive one or more of brain tissue electrodes 76 to apply deep brain stimulation (DBS) to deep brain structure 28, and (b) drive CSF electrode 78 and one or more of brain tissue electrodes 76 to clear a substance from brain parenchyma into the CSF-filled space.

For some applications, control circuitry 80 is configured to simultaneously (a) drive the one or more of brain tissue electrodes 76 to apply the DBS to deep brain structure 28, and (b) drive CSF electrode 78 and the one or more of brain tissue electrodes 76 to clear the substance from brain the brain parenchyma into the CSF-filled space. For some applications, the one or more of brain tissue electrodes 76 configured to apply the DBS and the one or more of brain tissue electrodes 76 configured to clear the substance include at least one common brain tissue electrode 76, e.g., entirely common brain tissue electrode(s) 76, while for other applications, the different electrodes are configured in non-overlapping sets.

For sonic applications, control circuitry 80 is configured to alternatingly (a) drive the one or more of brain tissue electrodes 76 to the DBS to deep brain structure 28, and (b) drive the CSF electrode and the one or more of brain tissue electrodes 76 to clear the substance from the brain parenchyma into the CSF-filled space. For some applications, the one or more of brain tissue electrodes 76 configured to apply the DBS and the one or more of brain tissue electrodes 76 configured to clear the substance include at least one common brain tissue electrode 76, e.g., entirely common brain tissue electrode(s) 76, while for other applications, the different electrodes are configured in non-overlapping sets.

Reference is made to FIG. 2A. For some applications. CSF electrode 78 is fixed to elongate support structure 74.

Reference is made to FIG. 2B. For some applications, electrical lead 72 is a first electrical lead 72A, and elongate support structure 74 is a first elongate support structure 74. Electrical brain treatment system 70 further comprises a second electrical lead 72B, which comprises a second elongate support structure 74B (e.g., having a length of at least 3 cm, no more than 25 cm, and/or between 3 and 25 cm). CSF electrode 78 is fixed to second elongate support structure 74B. Control circuitry 80 is electrically coupled to first and second electrical leads 72A and 72B.

For some applications, such as for treating Alzheimer's disease by the DBS, deep brain structure 28 is selected from the group consisting of: hippocampus 62 and fornix 64.

For some applications, such as for treating Parkinson's disease by the DBS, deep brain structure 28 is selected from the group consisting of: thalamus 60, a subthalamic nucleus (STN), a globus pallidus (GPi) (e.g., a pars interna of the GPi), an intermediate thalamus (VIM) in thalamus 60, caudal zona incerta, and pallidofugal fibers medial to the STN.

Figure 3:
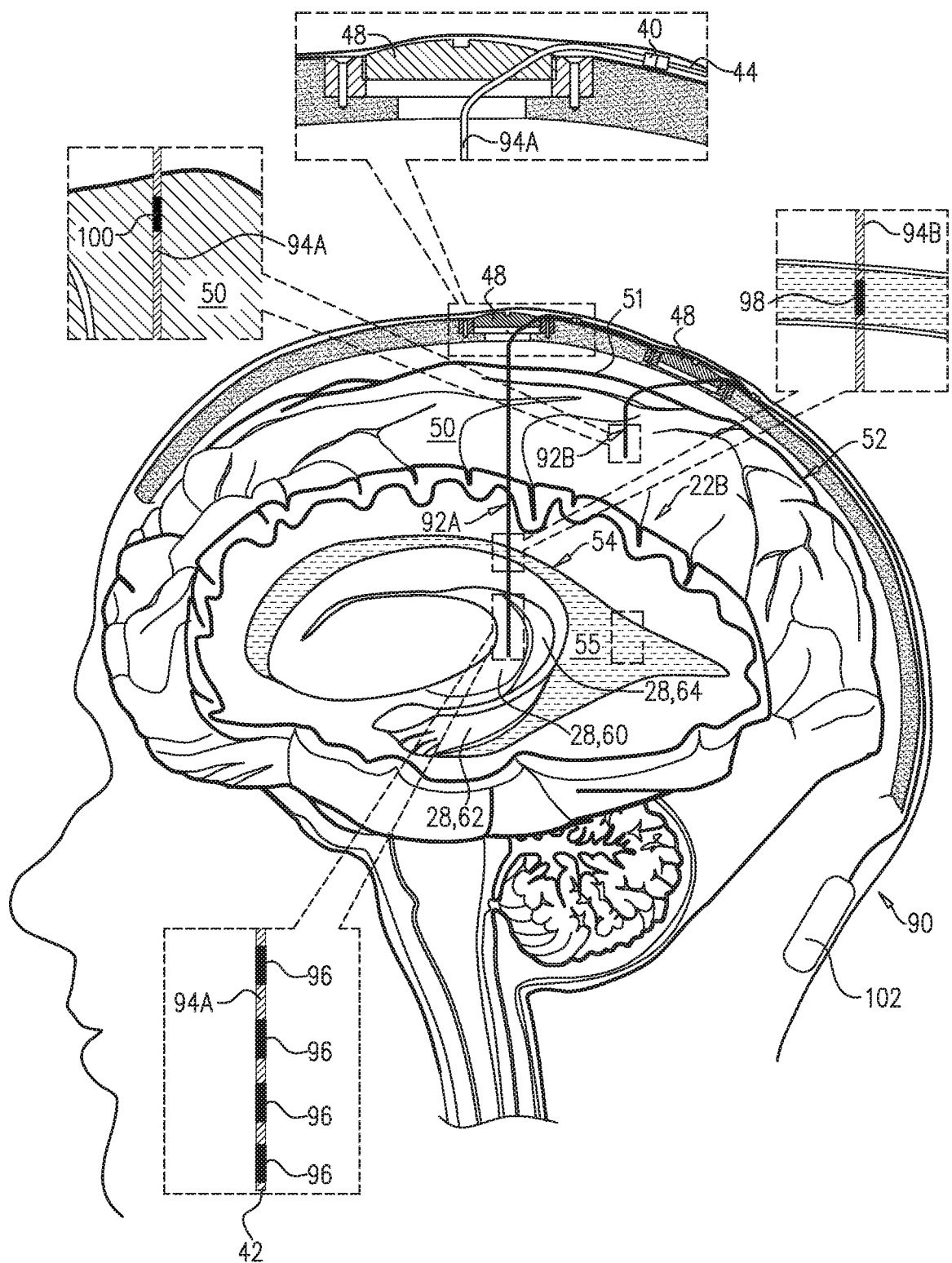
FIG. 3 is a schematic illustration of yet another electrical brain treatment system, in accordance with an application of the present invention.

Reference is now made to FIG. 3, which is a schematic illustration of an electrical brain treatment system 90, in accordance with an application of the present invention. Except as described below, electrical brain treatment system 90 may implement any of the features of electrical brain treatment system 20, described hereinabove with reference to FIGS. 1A-D.

Electrical brain treatment system 90 comprises a first electrical lead 92A and second electrical lead 92B, which are configured to be implanted in brain 52 of a subject identified as at risk of or suffering from at least one disease, such as the diseases described above with reference to FIGS. 1A-D.

First electrical lead 92A typically comprises:
a first elongate support structure 94A;
deep brain stimulation (DBS) electrodes 96, fixed to first elongate support structure 94A, and configured to be implanted in deep brain structure 28; and
a cerebrospinal fluid (CSF) electrode 98, fixed to first elongate support structure 94A, and configured to be implanted in a CSF-filled space of brain 52, the CSF-filled space selected from the group consisting of: ventricular system 54 and subarachnoid space 144.

Second electrical lead 92B comprises:
a second elongate support structure 94B; and
a parenchymal electrode 100, fixed to second elongate support structure 94B, and configured to be implanted in direct physical contact with brain tissue selected from the group consisting of brain parenchyma 50 (as shown) and meninges 51 of brain 52 (configuration not shown).

Electrical brain treatment system 90 further comprises control circuitry 102, which is electrically coupled to first and second electrical leads 92A and 92B, and which is typically configured to (a) drive DBS electrodes 96 to apply deep brain stimulation (DBS) to deep brain structure 28, and (b) drive parenchymal electrode 100 and CSF electrode 98 to clear a substance from brain parenchyma 50 into the CSF-filled space.

For some applications, DBS electrodes 96 and CSF electrode 98 are electrically coupled to control circuitry 102 via a proximal end of first elongate support structure 94A, and DBS electrodes 96 are fixed to first elongate support structure 94A near (e.g., within 3 cm, such as within 2 cm of) a distal end of first elongate support structure 94A. For some applications, CSF electrode 98 is fixed to first elongate support structure 94A proximal to a proximal-most one of DBS electrodes 96.

Although electrical brain treatment systems 20, 70, and 90 have been described herein as typically comprising DBS electrodes 26 or DBS electrodes 96 and control circuity configured to drive the DBS electrodes to apply DBS to a deep brain structure, for some applications electrical brain treatment systems 20, 70, and 90 do not comprise DBS electrodes and are not configured to apply DBS. In these applications, the electrical brain treatment systems may implement any of the other techniques described herein not directly related to DBS.

The following techniques may be used in combination with electrical brain treatment system 20, described hereinabove with reference to FIGS. 1A-D; electrical brain treatment system 70, described hereinabove with reference to FIGS. 2A-B; or electrical brain treatment system 90, described hereinabove with reference to FIG. 3;

when implementing the following techniques, electrical brain treatment systems 20, 70, and 90 may or may not comprise DBS electrodes and may or may not be configured to apply DBS. These techniques may also be used in combination with other electrical brain treatment systems, such as those described in PCT Publication WO 2017/006327 and/or PCT Publication WO 2017/072769, both of which are incorporated herein by reference.

For some applications, an electrical brain treatment system is provided that comprises:
a parenchymal electrode, configured to be implanted in direct physical contact with brain tissue of a subject identified as at risk of or suffering from a disease, the brain tissue selected from the group consisting of: brain parenchyma and meninges of the brain;
a cerebrospinal fluid (CSF) electrode, configured to be implanted in a CSF-filled space of the brain, the CSF-filled space selected from the group consisting of: a ventricular system and a subarachnoid space; and control circuitry.

For some applications, the control circuitry is configured to:

during amyloid-beta-clearance states, clear beta amyloid from the brain parenchyma into the CSF-filled space by applying direct current between the parenchymal electrode and the CSF electrode, with a negative charge at the parenchymal electrode and a positive charge at the CSF electrode, wherein the amyloid-beta-clearance states have an average duration of at least 5 minutes, and during metal-ion-clearance states, clear metal ions from the brain parenchyma into the CSF-filled space by applying direct current between the parenchymal electrode and the CSF electrode, with a positive charge the parenchymal electrode and a negative charge at the CSF electrode, wherein the metal-ion-clearance states have an average duration of at least 1 minute.

This technique clears both amyloid beta and metal ions, even though they have opposite charges. During the amyloid-beta-clearance states, a substantial amount of amyloid beta is cleared from the brain parenchyma. to the CSF-filled space. The CSF-filled space naturally clears the amyloid beta during the amyloid-beta-clearance states, so that amyloid beta does not build up in the CSF-filled space. As a result, during the metal-ion-clearance states, the applied current does not drive a substantial amount of amyloid beta back into the brain parenchyma.

For some applications, applying the current with the positive charge at the parenchymal electrode and the negative charge at the CSF electrode during the metal-ion-clearance states additionally has the same effect as applying the current with the second polarity opposite the first polarity, as described hereinabove, for example, releasing any material that may build up on the electrodes.

Typically, the control circuitry is configured to set an aggregate duration of the amyloid-beta-clearance states during a period to equal at least 4 times (e.g., at least 9 times) an aggregate duration of the metal-ion-clearance states during the period, the period having a duration of at least 30 days. Typically, the control circuitry is configured to set the aggregate duration of the amyloid-beta-clearance states during the period to equal to no more than 100 times the aggregate duration of the metal-ion-clearance states during the period.

For some applications, the control circuitry is configured to set the average duration of the amyloid-beta-clearance states to be at least one hour and/or less than 8 hours. For example, the control circuitry may be configured to clear amyloid beta for between 4 and 8 hours per day, such as during nighttime. Alternatively or additionally, for some applications, the control circuitry is configured to set the average duration of the metal-ion-clearance states to be at least 2 minutes and/or less than one hour. For example, the control circuitry may be configured to clear the metal ions for between 15 minutes and one hour, e.g., 30 minutes, per day, optionally during relatively small time periods, e.g., having a duration of one to 10 minutes, e.g., one to 5 minutes each.

For some applications, the control circuitry is configured to assume the amyloid-beta-clearance states during nighttime, and the metal-ion-clearance states during daytime. As mentioned above, the control circuitry may be driven by an external controller that is in wireless or wired communication with the control circuitry, and the external controller may be mounted on a bed of the subject (e.g., disposed within a mattress), and may be configured to activate the control circuitry only at night, and/or only when the subject is sleeping. Such nighttime activation may to some degree mimic the natural timing of clearance of the amyloid beta during sleep, during which the extracellular spaces are wider than during wakefulness, which allows more interstitial fluid (ISF) flow within the brain For some applications, the control circuitry is configured to assume respective rest states after concluding the amyloid-beta-clearance states before beginning the respective subsequent metal-ion-clearance states. For example, an average duration of the rest states may be at least 5 minutes.

For some applications in which control circuitry 34 is configured to apply direct current, the control circuitry is configured to apply the direct current with a first average strength during the amyloid-beta-clearance states and a second average strength during the metal-ion-clearance states, the first average strength equal to at least 150% of the second average strength. For some applications in which control circuitry 34 is configured to apply current predominantly with a first polarity, the control circuitry is configured to apply the current with the first polarity with a first average strength during the amyloid-beta-clearance states and a second average strength during the metal-ion-clearance states, the first average strength equal to at least 150% of the second average strength.

For some applications in which control circuitry 34 is configured to apply direct current, the control circuitry is configured to drive the parenchymal electrode and the CSF electrode to apply the direct current as a series of pulses during the amyloid-beta-clearance states. For some applications, the control circuitry is configured to apply the direct pulses with an average amplitude of at least 0.25 mA, no more than 0.5 mA, and/or between 0.25 and 0.5 mA, an average pulse width of at least 0.5 ms, no more than 2 ms, and/or between 0.5 and 2 ms, and an average frequency of at least 1 Hz, no more than 5 Hz, and/or between 1 and 5 Hz (e.g., between 1.5 and 3 Hz, such as between 1.5 and 2.5 Hz). For some applications in which control circuitry 34 is configured to apply current predominantly with a first polarity, the control circuitry is configured to drive the parenchymal electrode and the CSF electrode to apply the current as a series of pulses during the amyloid-beta-clearance states. For some applications, the control circuitry is configured to (a) apply the pulses with the first polarity with an average amplitude of at least 0.25 mA, no more than 0.5 mA, and/or between 0.25 and 0.5 mA, an average pulse width of at least 0.5 ms, no more than 2 ms, and/or between 0.5 and 2 ms, and an average frequency of at least 1 Hz, no more than 5 Hz, and/or between 1 and 5 Hz, and/or (h) apply the pulses with the second polarity with an average amplitude of at least 0.01 mA (e.g., at least 0.025 mA), no more than 0.1 mA (e.g., no more than 0.05 mA), and/or between 0.01 mA (e.g., 0.025 mA) and 0.1 mA (e.g., 0.05 mA), an average pulse width of at least 0.025 ms (e.g., at least 0.05 ms), no more than 0.4 ms (e.g., no more than 0.2 ms), and/or between 0.025 ms (e.g., 0.05 ms) and 0.4 ms (e.g., 0.2 ms), and an average frequency of at least 1 Hz, no more than 5 Hz, and/or between 1 and 5 Hz.

Figure 4:
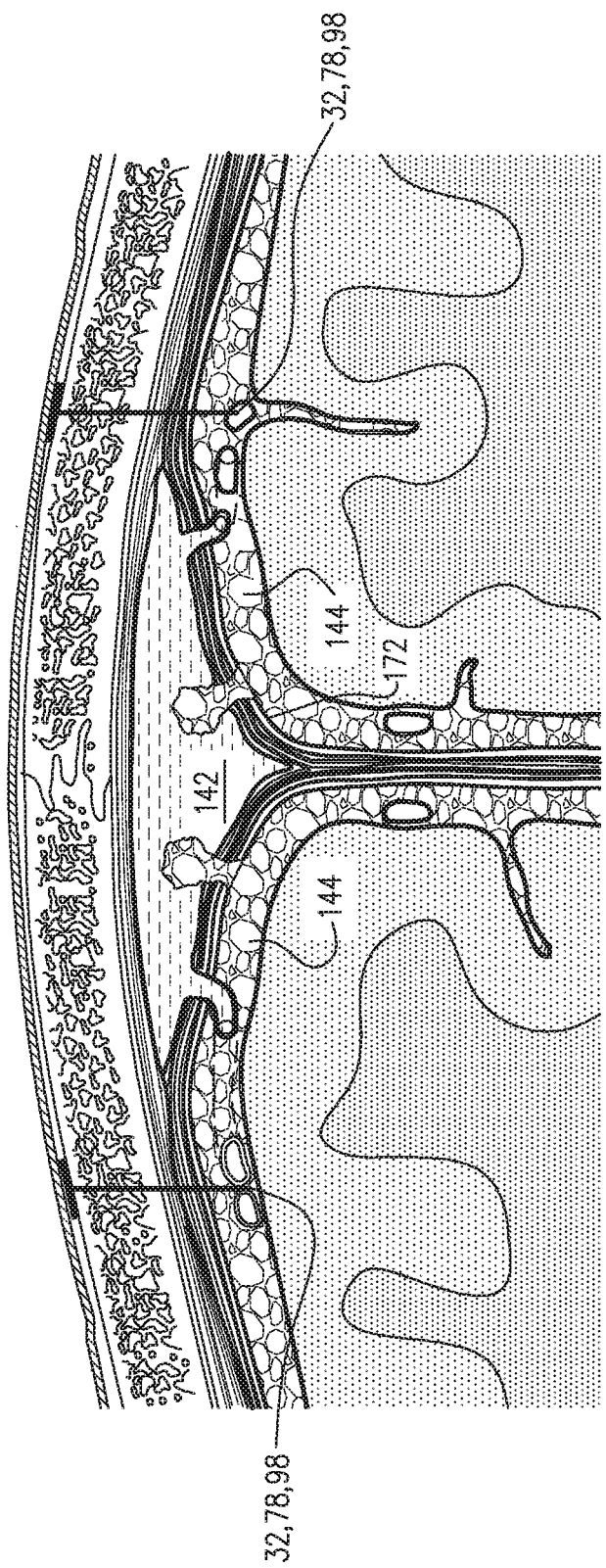
FIG. 4 is a schematic illustration of implantation of a cerebrospinal fluid (CSF) electrode in a subarachnoid space, in accordance with an application of the present invention.

Reference is now made to FIG. 4, which is a schematic illustration of implantation of CSF electrode 32 in subarachnoid space 144, in accordance with an application of the present invention. FIG. 4 is an anterior view of brain 52. For any of the applications described herein, CSF electrode 32, 78, or 98 may implanted in subarachnoid space 144 (which is in fluid communication with ventricular system 54 because CSF drains into cisterns of subarachnoid space 144 via foramina of ventricular system 54).

For any of the applications described herein, the electrical brain treatment system may be configured to, in addition to clearing the substance (e.g., the amyloid beta, the metal ions, the tau protein, and/or the waste substance) from brain parenchyma 50 into the CSF-filled space, clear the substance from the CSF-filled space (e.g., subarachnoid space 144) to a superior sagittal sinus 142 (labeled in FIG. 4). These applications may implement, mutatis mutandis, techniques described in above-mentioned WO 2017/072769, with reference to FIGS. 4A-G thereof.

For some of these applications, control circuitry 34 is configured to simultaneously drive electrodes to both (a) clear the substance from brain parenchyma 50 into the CSF-filled space, and (b) clear the substance from the CSF-filled space to superior sagittal sinus 142. For example, control circuitry 34 may be configured to apply different respective voltages to parenchymal electrode 30, CSF electrode 32, and a midplane treatment electrode.

For others of these applications, control circuitry 34 is configured to alternatingly drive sets of the electrodes, such as (a) during a plurality of first time periods, driving parenchymal electrode 30 and CSF electrode 32, in order to clear the substance from brain parenchyma 50 into the CSF-filled space, and (b) during a plurality of second time periods, typically not overlapping with the first time periods, driving midplane treatment electrode and either CSF electrode 32 or another electrode, in order to clear the substance from the CSF-filled space to superior sagittal sinus 142.

Figure 5A:
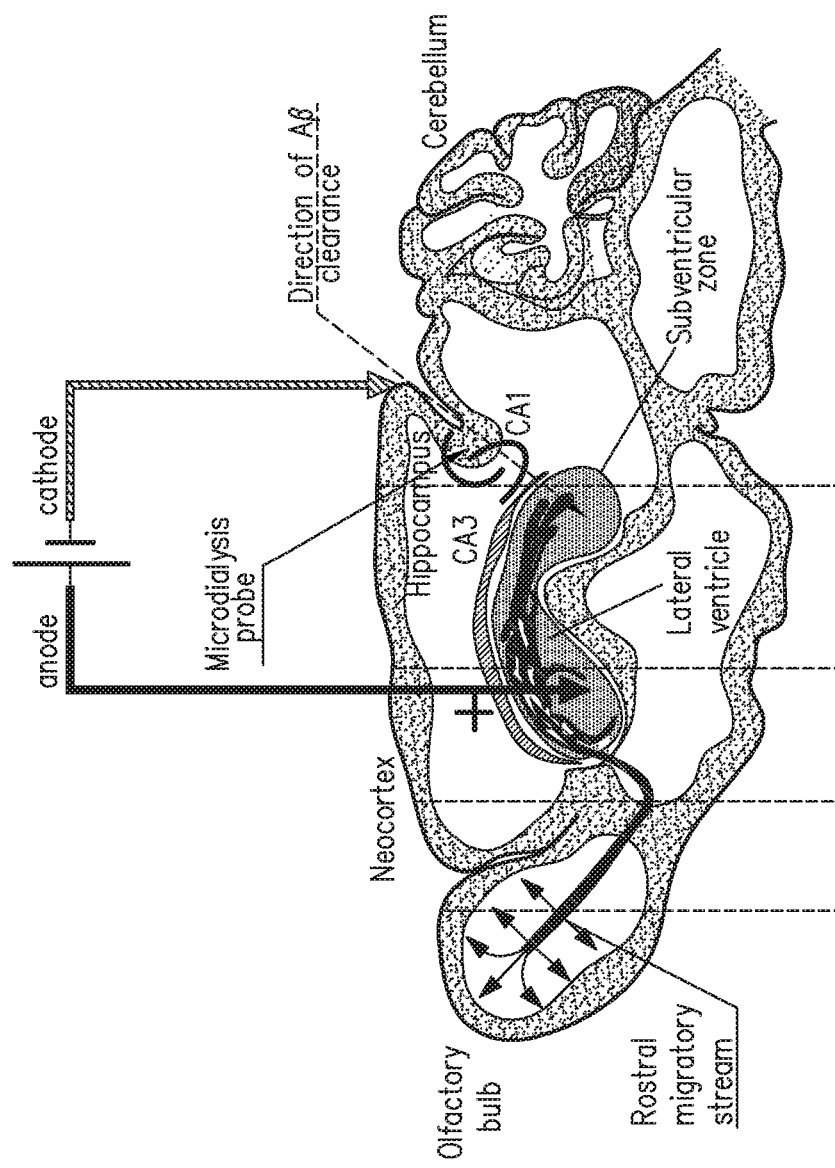
FIGS. 5A-D show results of an animal experiment performed on behalf of the inventors, in accordance with an application of the present invention.

Reference is made to FIGS. 5A-D, which show results of an animal experiment performed on behalf of the inventors, in accordance with an application of the present invention. Four 2-3 month old APP/PS1+/− mice were stereotaxically implanted with unilateral guide cannula above the hippocampus at bregma −3.1, midline −2.5, and tip at dura −1.2 mm using techniques similar to those described in Cirrito et al., "In vivo assessment of brain interstitial fluid with microdialysis reveals plaque-associated changes in amyloid-beta metabolism and half-life," J Neurosci. 2003 Oct. 1;23 (26):8844-53 ("Cirrito et al. 2003") and Cirrito et al., "Endocytosis is required for synaptic activity-dependent release of amyloid.-beta in vivo," Neuron. 2008 Apr. 10; 58(1): 42-51 ("Cirrito et al. 2008"), both of which are incorporated herein by reference. As shown in FIG. 5A, a negative electrode was implanted into parenchyma at the cortical surface and a positive electrode was implanted in the lateral ventricle. The electrode wires were soldered directly to gold male pins. A guide cannula and the electrodes were secured to the skull and insulated using dental cement. The ventricular electrode comprised between 2 and 6 twisted Teflon-coated stainless-steel wires (bare diameter 0.003"). The parenchymal electrode comprised a tungsten rod (D=0.25 mm, L=2 cm). At the end of the electrode a sphere was formed using a laser to achieve good current distribution and to avoid brain lesions. The electrode was then coated using Parylene C (except the connector and the sphere at the tip). Finally, the sphere was coated using Amplicoat, designed to enhance communication at the interface between human tissue and a stimulation (Heraeus Group, Hanau, Germany).

Following implantation of the electrodes, the mice recovered for 5-7 days in a RaTurn cage to re-established their normal sleep-wake patterns on a 12-12 light-dark cycle. After the recovery period, each mouse was briefly anesthetized and an in vivo microdialysis probe having a 38 kDa molecular weight cutoff (MWCO) membrane (Bioanalytical Systems, West Lafayette, Ind., USA)) was inserted into the hippocampus. During each trial, the mice were housed in specially-designed RaTurn cages to provide them freedom of movement and ad lib food and water. After a 12-15 hour recovery time, baseline interstitial fluid (ISF) arnyloid-beta levels were measured every 60 to 90 minutes for 24 hours (20 samples in 24 hours) to establish the diurnal rhythm in ISF amyloid-beta fluctuations.

Start time was 8 a.m. at the beginning of the light phase. After the 24-hour baseline period (without application of current), the electrical protocol was applied continuously for 24 hours with sampling of ISF amyloid beta. The following parameters were used: pulsed direct current (DC); amplitude: 0.3 mA; pulse width: 1 ms; and frequency: 2 Hz. Assessment of arnyloid beta clearance was performed by measuring the concentration of amyloid beta in the interest of region in the electrical field every hour for 24 hours, using the microdialysis probe and an external monitor. For each animal, ISF A$\beta$ levels were normalized to the average basal ISF amyloid beta concentration (mean of 24 hours of collection during no treatment). Mean amyloid beta levels were calculated for a full 24 hours, as well as separately during the light (sleep) and dark (wake) phases.

Figure 5B:
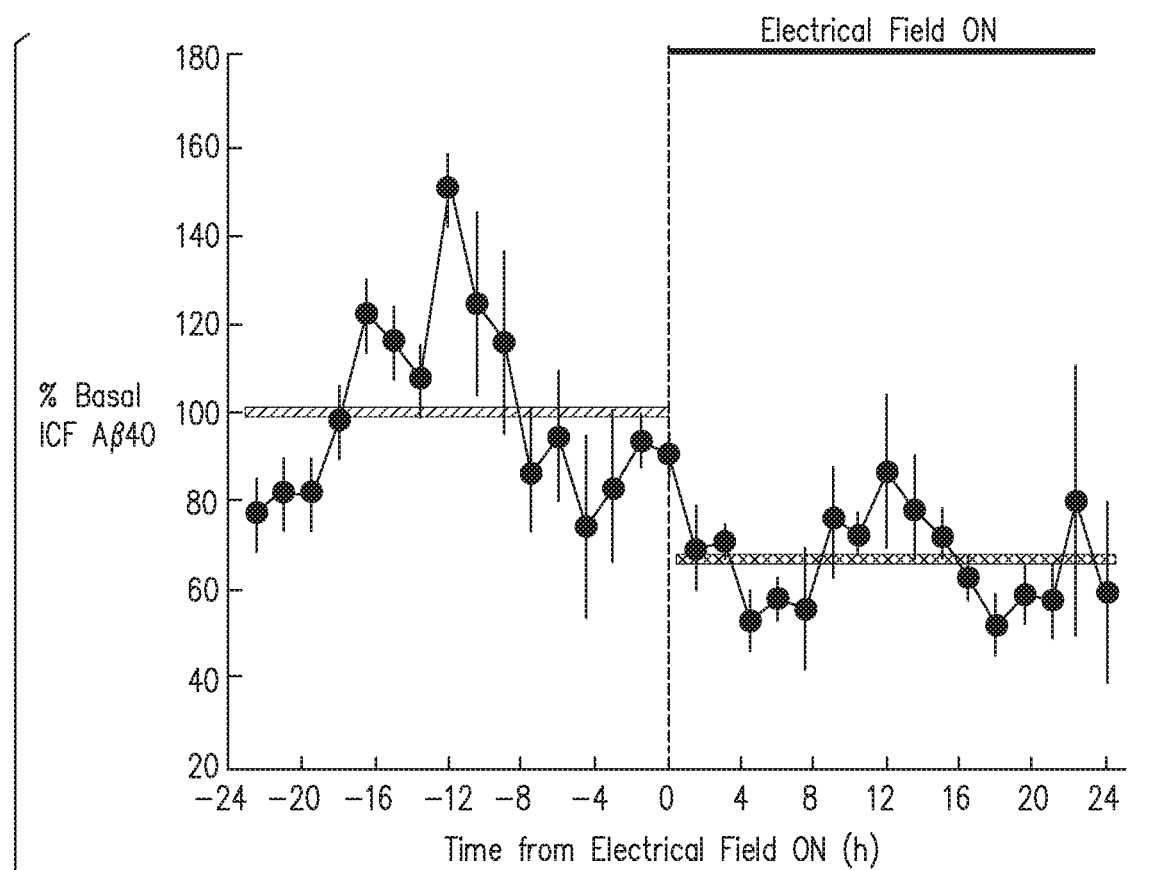
Figure 5B:
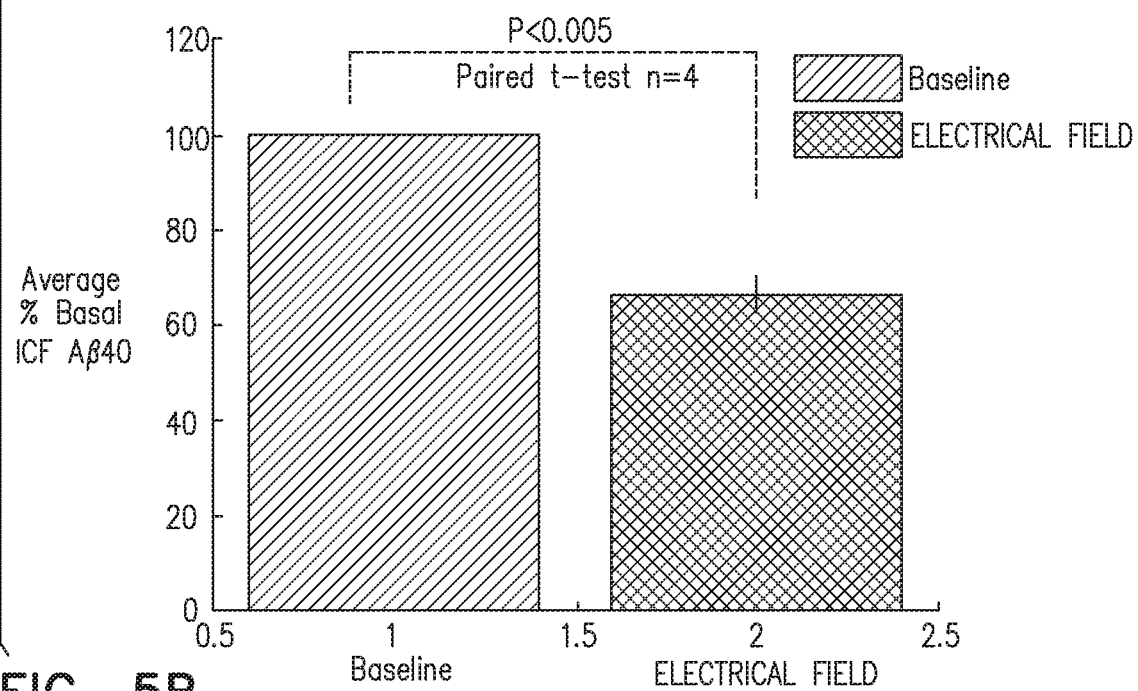
Figure 5C:
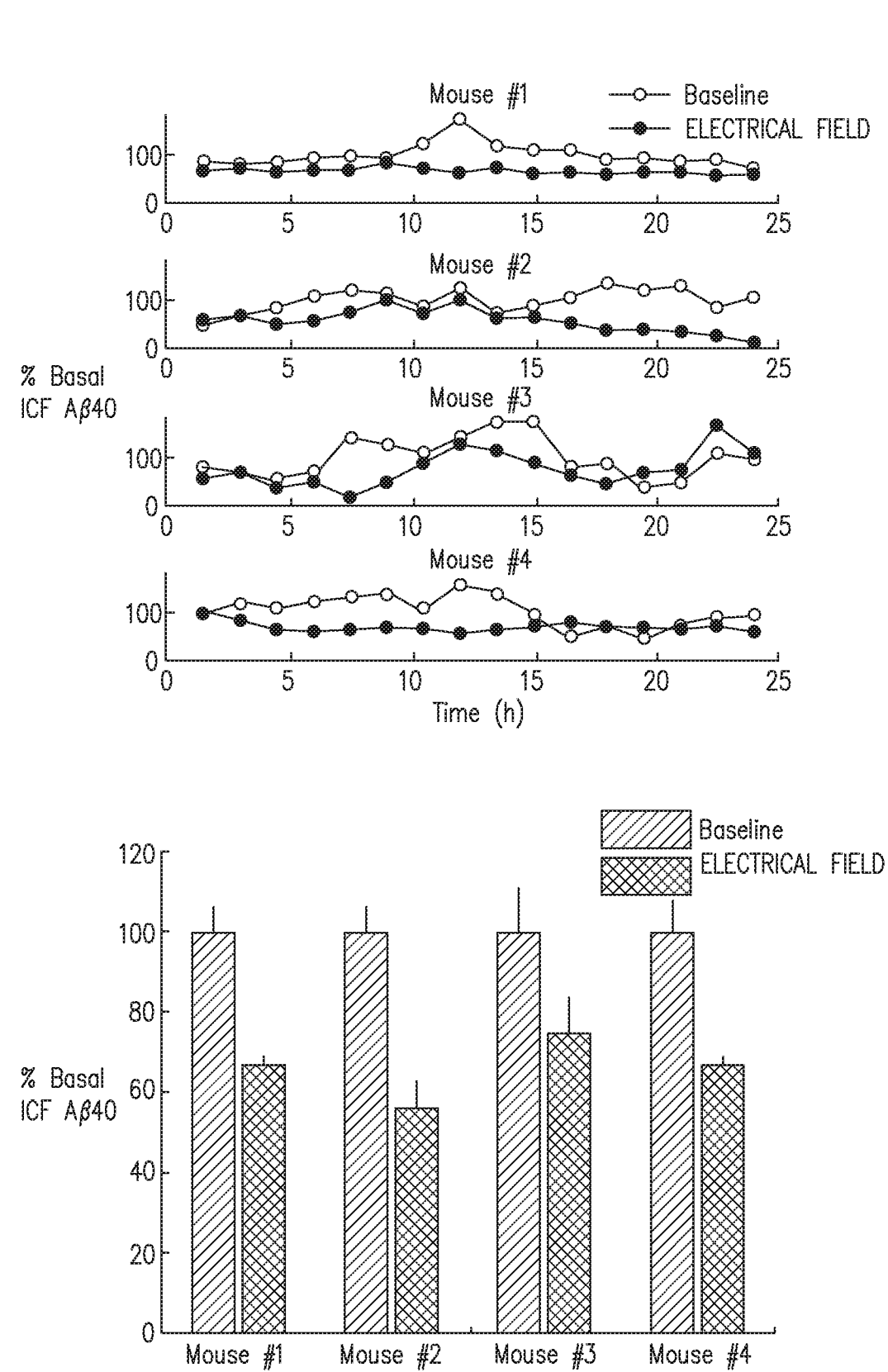
Figure 5D:
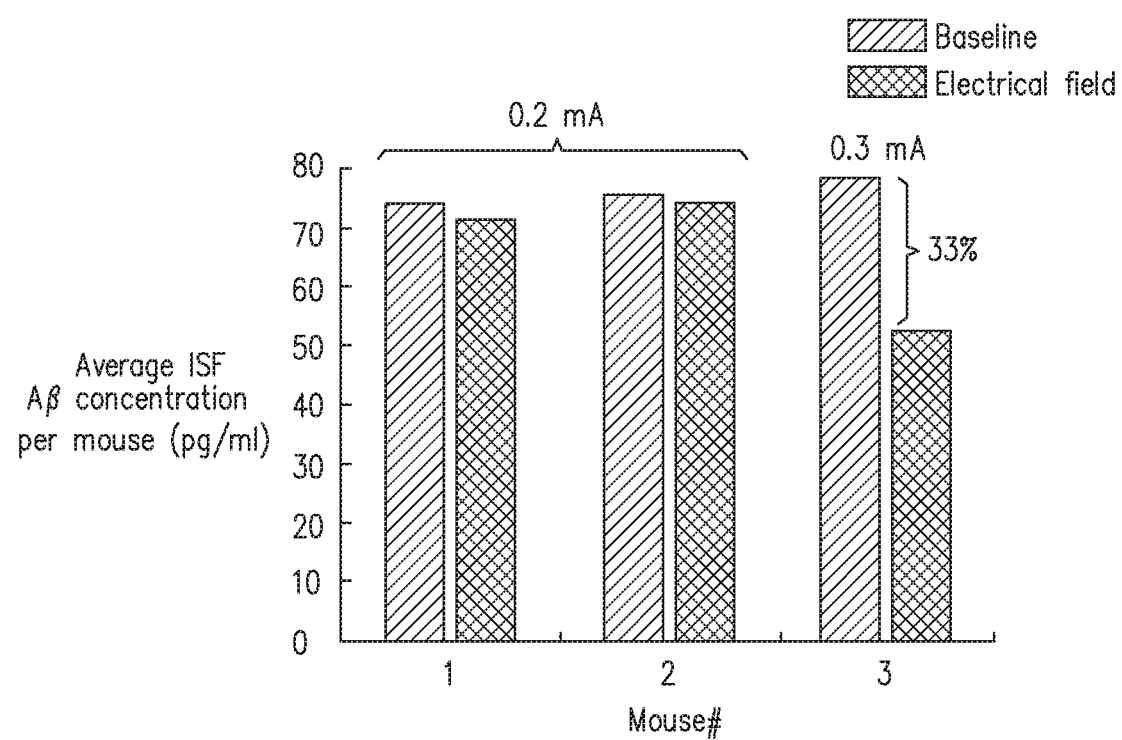

As shown in FIGS. 5B and 5C, application of the electrical current resulted in a significant reduction in amyloid beta concentration in the parenchyma of the hippocampus. In addition to an amplitude of 0.3 mA, as discussed above, an amplitude of 0.2 mA was also assessed, and found not to result in a reduction in amyloid beta concentration in the parenchyma of the hippocampus, as shown in FIG. 5D, thereby demonstrating that amyloid beta clearance is dose-dependent.

After completion of the electrical protocol, histological analysis was performed. During collection, ISF samples were stored in a refrigerated fraction collector. At the conclusion of each trial, A$\beta$x-40 was measured by sandwich ELISA using techniques similar to those described by Bero et al., "Neuronal activity regulates the regional vulnerability to amyloid-beta deposition," Nature Neuroscience, June 2011, pp. 750-758. Animals were sacrificed by perfusion with chilled PBS-heparin, followed by post-fixation in 4% paraformaldehyde for 24 hours then processed for histology to assess tissue morphology by cresyl violet staining. ISF A$\beta$x-40 levels were determined by sandwich ELISA using a A$\beta$40-specific antibody (mHJ2) to capture followed by a biotinylated central domain anti-A$\beta$ antibody (mHF5.1) for detection, using techniques similar to those described by Cirrito et al. 2011. It was found that the electrical protocol did not result in any brain lesions.

The following techniques may be used in combination with electrical brain treatment system 20, described hereinabove with reference to FIGS. 1A-D; electrical brain treatment system 70, described hereinabove with reference to FIGS. 2A-B; or electrical brain treatment system 90, described hereinabove with reference to FIG. 3. These techniques may also be used in combination with other electrical brain treatment systems, such as those described in PCT Publication WO 2017/006327, which entered the U.S. national stage as U.S. application Ser. No. 15/742,245 on Jan. 5, 2018 and published as U.S. Patent Application Publication 2018/0193633, and/or PCT Publication WO 2017/072769, which entered the U.S. national stage as U.S. application Ser. No. 15/771,551 on Apr. 27, 2018 and published as U.S. Patent Application Publication 2019/0076653, both of which are incorporated herein by reference.

For some applications, an electrical brain treatment system is provided that comprises:
- a parenchymal electrode, configured to be implanted in direct physical contact with brain tissue of a subject identified as at risk of or suffering from a disease, the brain tissue selected from the group consisting of: brain parenchyma and meninges of brain 52;
- a cerebrospinal fluid (CSF) electrode, configured to be implanted in a CSF-filled space of a brain of the subject, the CSF-filled space selected from the group consisting of: a ventricular system and a subarachnoid space; and
- control circuitry.

The control circuitry is configured to clear a substance from brain parenchyma 50 into the CSF-filled space of brain 52 by applying direct current between parenchymal electrode 30 and CSF electrode 32 as a series of pulses, with the parameters described in the following bullets and paragraphs. Alternatively, the control circuity is configured to apply current between parenchymal electrode 30 and CSF electrode 32 predominantly with a first polarity, but also partially with a second polarity opposite the first polarity, such as described hereinabove (optionally including the parameters described hereinabove); in this case, the parameters described in the following bullets and paragraphs apply to the current applied with the first polarity.
- an average amplitude of between 0.25 and 0.5 mA, such as between 0.28 and 0.4 mA, e.g., between 0.28 and 0.35 mA,
- an average pulse width of between 0.5 and 2 ms, such as between 0.8 and 1.2 ms, and
- an average frequency of between 1 and 5 Hz, such as 1.5 and 3 Hz, e.g., between 1.5 and 2.5 Hz.

For some applications, the control circuitry is configured to apply the direct current with an average amplitude of between 0.28 and 0.35 mA, an average pulse width of between 0.8 and 1.2 ms, and an average frequency of between 1.5 and 2.5 Hz.

For some applications, the control circuitry is configured to apply the direct current as the series of pulses with a duty cycle of between 1% and 30%.

For some applications, the control circuitry is configured to apply the direct current using an average voltage of less than 1.2 V.

For some applications, control circuitry 34 is activated to apply the voltage intermittently with a preprogrammed frequency and/or duty cycle. These parameters may be (a) applicable to all patients or a subgroup of patients, (b) set during a calibration procedure upon implantation of the electrodes, or (c) set based on a geometry of placement of parenchymal and/or CSF electrodes 30 and/or 32.

Alternatively, control circuitry 34 is configured to set these parameters in real time by sensing the current resulting from the applied voltage.

For some applications, control circuitry 34 is activated to measure the current resulting from the applied voltage during each of the applied pulses, and to terminate each of the applied pulses when the magnitude of the measured current falls below a threshold value. For example, the threshold value may be a preprogrammed constant, or may be based on (e.g., a percentage of) the initial current magnitude measured upon commencement of the respective pulse. Control circuitry 34 waits during a discharge period before applying the next pulse.

As used in the present application, including the claims, "treating" includes both treating a subject already diagnosed with one or more diseases (such as by delaying, slowing, or reversing progression of the one or more diseases, e.g., in a patient diagnosed at an early stage), as well as preventing the development of one or more diseases in a subject not diagnosed with the disease and/or asymptomatic for the disease. For example, the techniques described herein may be used to prevent or delay the development of Alzheimer's disease and/or CAA in responsive to detection of an abnormal level of amyloid beta, such as using a blood test or a spinal tap.

For some applications, control circuitry 34 is activated to drive the parenchymal and the CSF electrodes in sessions, each of which has a duration of several seconds or several minutes, or continuously for longer periods (e.g., 30 minutes). For some applications, the electrodes are not driven for a period that is at least an hour. Optionally, control circuitry 34 is activated to drive the electrodes only when the subject is sleeping, such as to take advantage of the widening of extracellular spaces and/or to inhibit any sensations that may be associated with the driving. For example, control circuitry 34 may be activated to use one or more of the electrodes as EEG electrodes to detect sleep. For some applications, power for activating and/or charging control circuitry 34 is transmitted from a wireless energy transmitter in a device applied to the head, such as a hat, or from a wireless energy transmitter in, under, or above a mattress, such as described hereinabove. For some applications, control circuitry 34 is activated to drive the electrodes according to a pre-selected schedule, such as a duty cycle, such as for a few hours per day. For example, control circuitry 34 may be configured to be controlled and/or powered by an extracorporeal control circuitry, such as a control circuitry comprising a wireless transmitter, disposed in and/or in the vicinity of the subject's bed. For some applications, one or more rest periods during which the control circuitry does not drive the electrodes are provided in the pre-selected schedule.

The scope of the present invention includes embodiments described in the following applications, which are assigned to the assignee of the present application and are incorporated herein by reference. In an embodiment, techniques and apparatus described in one or more of the following applications are combined with techniques and apparatus described herein: U.S. Pat. No. 9,731,122 to Gross; U.S. Pat. No. 9,616,221 to Gross; PCT Publication WO 2017/006327 to Gross; U.S. Pat. No. 9,724,515 to Fostick et al.; PCT Publication WO 2017/072769 to Fostick et al.; U.S. patent application Ser. No. 15/864,065, filed Jan. 8, 2018, which published as U.S. Patent Application 2018/0193646; and U.S. Application 62/500,747, filed May 3, 2017.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus comprising an electrical brain treatment system, which comprises:
   a first electrode, configured to be implanted in a cerebrospinal fluid (CSF)-filled space of a brain of a subject identified as at risk of or suffering from a disease, the CSF-filled space selected from the group consisting of: a ventricular system of the brain and a subarachnoid space;

a second electrode, configured to be implanted superficial to brain parenchyma of the brain, such that the brain parenchyma is spatially disposed between the ventricular system of the brain and the second electrode; and control circuitry, which is electrically coupled to the first and the second electrodes, and which is configured to clear a substance from the brain parenchyma into the CSF-filled space of the brain by:

applying current between the first and the second electrodes as a series of pulses, configuring at least 80% and less than 100% of a charge of the current to have a first polarity and the remainder of the charge of the current to have a second polarity opposite the first polarity, and applying the pulses with the first polarity with an average amplitude of between 0.25 and 0.5 mA, an average pulse width of between 0.5 and 2 ms, and an average frequency of between 1 and 5 Hz.

2. The apparatus according to claim 1, wherein the control circuitry is configured to configure at least 90% of the charge of the current to have the first polarity and the remainder of the charge of the current to have the second polarity opposite the first polarity.

3. The apparatus according to claim 1, wherein the control circuitry is configured to apply the current with the second polarity with an average frequency equal to no more than 20% of the average frequency of the pulses with the first polarity.

4. The apparatus according to claim 1, wherein the average frequency is between 1.5 and 3 Hz, and wherein the control circuitry is configured to apply the current with the first polarity with the average frequency of between 1.5 and 3 Hz.

5. The apparatus according to claim 1,
wherein the average amplitude is between 0.28 and 0.35 mA, the average pulse width is between 0.8 and 1.2 ms, and the average frequency is between 1.5 and 2.5 Hz, and
wherein the control circuitry is configured to apply the current with the first polarity with the average amplitude of between 0.28 and 0.35 mA, the average pulse width of between 0.8 and 1.2 ms, and the average frequency of between 1.5 and 2.5 Hz.

6. The apparatus according to claim 1, wherein the control circuitry is configured to apply the current with the first polarity using an average voltage of less than 1.2 V.

7. The apparatus according to claim 1, wherein the disease is Alzheimer's disease, and wherein the second electrode is configured to be implanted in the subject identified as at risk of or suffering from Alzheimer's disease.

8. The apparatus according to claim 1, wherein the disease is cerebral amyloid angiopathy (CAA), and wherein the second electrode is configured to be implanted in the subject identified as at risk of or suffering from CAA.

9. The apparatus according to claim 1, wherein the CSF-filled space of the brain is the ventricular system, and wherein the first electrode is a ventricular electrode, configured to be implanted in the ventricular system.

10. The apparatus according to claim 1, wherein the CSF-filled space of the brain is the subarachnoid space, and wherein the first electrode is a subarachnoid electrode, configured to be implanted in the subarachnoid space.

11. The apparatus according to claim 1, wherein the substance includes amyloid beta, and wherein the control circuitry is configured to drive the first and the second electrodes to clear the amyloid beta from the brain parenchyma into the CSF-filled space of the brain.

12. The apparatus according to claim 1, wherein the substance includes tau protein, and wherein the control circuitry is configured to drive the first and the second electrodes to clear the tau protein from the brain parenchyma into the CSF-filled space of the brain.

13. The apparatus according to claim 1, wherein the current is non-excitatory, and wherein the control circuitry is configured to drive the first and the second electrodes to clear the substance by applying the non-excitatory current between the first and the second electrodes.

14. The apparatus according to claim 1, wherein the second electrode is configured to be implanted in direct physical contact with brain tissue of the brain selected from the group consisting of: the brain parenchyma and meninges of the brain.

15. The apparatus according to claim 14, wherein the second electrode is configured to be implanted within the brain parenchyma.

16. The apparatus according to claim 14, wherein the second electrode is configured to be implanted in direct physical contact with the meninges of the brain.

17. A method comprising:
implanting a first electrode of an electrical brain treatment system in a cerebrospinal fluid (CSF)-filled space of a brain of a subject identified as at risk of or suffering from a disease selected from the group consisting of Alzheimer's disease and cerebral amyloid angiopathy (CAA), the CSF-filled space selected from the group consisting of: a ventricular system of the brain and a subarachnoid space;

implanting a second electrode of the electrical brain treatment system superficial to brain parenchyma of the brain, such that the brain parenchyma is spatially disposed between the ventricular system of the brain and the second electrode; and activating control circuitry, which is electrically coupled to the first and the second electrodes, to clear a substance from the brain parenchyma into the CSF-filled space of the brain by applying direct current between the first and the second electrodes as a series of pulses, with an average amplitude of between 0.25 and 0.5 mA, an average pulse width of between 0.5 and 2 ms, and an average frequency of between 1 and 5 Hz, the substance selected from the group of substances consisting of amyloid beta and tau protein.

18. The method according to claim 17, wherein the disease is Alzheimer's disease, and wherein implanting the first electrode comprises implanting the first electrode in the CSF-filled space of the brain of the subject suffering from Alzheimer's disease.

19. The method according to claim 17, wherein the disease is CAA, and wherein implanting the first electrode comprises implanting the first electrode in the CSF-filled space of the brain of the subject suffering from CAA.

20. The method according to claim 17, wherein the CSF-filled space of the brain is the ventricular system, and wherein implanting the first electrode comprises implanting the first electrode in the ventricular system.

21. The method according to claim 17, wherein the CSF-filled space of the brain is the subarachnoid space, and wherein implanting the first electrode comprises implanting the first electrode in the subarachnoid space.

22. The method according to claim 17, wherein implanting the second electrode superficial to the brain parenchyma comprises implanting the second electrode in direct physical contact with brain tissue of the brain selected from the group consisting of: the brain parenchyma and meninges of the brain.

23. The method according to claim 17, wherein the substance includes the amyloid beta, and wherein activating the control circuitry to clear the substance comprises activating the control circuitry to clear the amyloid beta from the brain parenchyma into the CSF-filled space.

24. The method according to claim 17, wherein the substance includes the tau protein, and wherein activating the control circuitry to clear the substance comprises activating the control circuitry to clear the tau protein from the brain parenchyma into the CSF-filled space.

25. The method according to claim 17, wherein the current is non-excitatory, and wherein activating the control circuitry comprises activating the control circuitry to clear the substance by applying the non-excitatory current between the first and the second electrodes.

26. The method according to claim 17, wherein the average frequency is between 1.5 and 3 Hz, and wherein activating the control circuitry comprises activating the control circuitry to clear the substance by applying the direct current with the average frequency of between 1.5 and 3 Hz.

27. The method according to claim 17,
wherein the average amplitude is between 0.28 and 0.35 mA, the average pulse width is between 0.8 and 1.2 ms, and the average frequency is between 1.5 and 2.5 Hz, and
wherein activating the control circuitry comprises activating the control circuitry to clear the substance by applying the direct current with the average amplitude of between 0.28 and 0.35 mA, the average pulse width of between 0.8 and 1.2 ms, and the average frequency of between 1.5 and 2.5 Hz.

28. The method according to claim 17, wherein activating the control circuitry comprises activating the control circuitry to clear the substance by applying the direct current using an average voltage of less than 1.2 V.

29. A method comprising:
implanting a first electrode of an electrical brain treatment system in a cerebrospinal fluid (CSF)-filled space of a brain of a subject identified as at risk of or suffering from a disease selected from the group consisting of Alzheimer's disease and cerebral amyloid angiopathy (CAA), the CSF-filled space selected from the group consisting of: a ventricular system of the brain and a subarachnoid space;
implanting a second electrode of the electrical brain treatment system superficial to brain parenchyma of the brain, such that the brain parenchyma is spatially disposed between the ventricular system of the brain and the second electrode; and
activating control circuitry, which is electrically coupled to the first and the second electrodes, to clear a substance from the brain parenchyma into the CSF-filled space of the brain by:
applying current between the first and the second electrodes as a series of pulses,
configuring at least 80% and less than 100% of a charge of the current to have a first polarity and the remainder of the charge of the current to have a second polarity opposite the first polarity, and
applying the pulses with the first polarity with an average amplitude of between 0.25 and 0.5 mA, an average pulse width of between 0.5 and 2 ms, and an average frequency of between 1 and 5 Hz.

30. The method according to claim 29,
wherein the average amplitude is between 0.28 and 0.35 mA, the average pulse width is between 0.8 and 1.2 ms, and the average frequency is between 1.5 and 2.5 Hz, and
wherein activating the control circuitry comprises activating the control circuitry to clear the substance by applying the current with the first polarity with the average amplitude of between 0.28 and 0.35 mA, the average pulse width of between 0.8 and 1.2 ms, and the average frequency of between 1.5 and 2.5 Hz.

31. The method according to claim 22, wherein implanting the second electrode in direct physical contact with the brain tissue comprises implanting the second electrode within the brain parenchyma.

32. The method according to claim 22, wherein implanting the second electrode in direct physical contact with the brain tissue comprises implanting the second electrode in direct physical contact with the meninges of the brain.

* * * * *